(12) United States Patent
Anderson

(10) Patent No.: US 7,806,910 B2
(45) Date of Patent: Oct. 5, 2010

(54) MULTI-ELEMENT BIASED SUTURE CLIP

(75) Inventor: Steven C. Anderson, Mountain View, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/461,323

(22) Filed: Jul. 31, 2006

(65) Prior Publication Data
US 2006/0265012 A1 Nov. 23, 2006

Related U.S. Application Data

(63) Continuation of application No. 10/305,923, filed on Nov. 26, 2002, now Pat. No. 7,108,710.

(51) Int. Cl.
*A61B 17/04* (2006.01)
(52) U.S. Cl. .................. 606/232; 24/132 R; 24/129 D
(58) Field of Classification Search .................. 606/232, 606/72, 74; 24/67.3, 132 R; 132/137, 151, 132/153, 145, 277, 279
See application file for complete search history.

(56) References Cited

U.S. PATENT DOCUMENTS

| 287,046 | A | | 10/1883 | Norton |
|---|---|---|---|---|
| 438,400 | A | | 10/1890 | Brennen |
| 1,088,393 | A | | 2/1914 | Backus |
| 1,331,401 | A | | 2/1920 | Summers |
| 1,426,111 | A | * | 8/1922 | Sacker .................. 132/153 |
| 1,516,990 | A | * | 11/1924 | Silverman .................. 132/150 |
| 1,596,004 | A | | 8/1926 | De Bengoa |
| 1,847,347 | A | * | 3/1932 | Maisto .................. 132/153 |
| 2,087,074 | A | | 7/1937 | Tucker |
| 2,254,620 | A | | 9/1941 | Miller |
| 2,316,297 | A | | 4/1943 | Southerland et al. |

(Continued)

FOREIGN PATENT DOCUMENTS

CA       2 339 060      2/2000

(Continued)

OTHER PUBLICATIONS

U.S. Appl. No. 60/696,069, filed Jul. 1, 2005, Pantages et al.

(Continued)

*Primary Examiner*—Todd E Manahan
*Assistant Examiner*—Diane Yabut
(74) *Attorney, Agent, or Firm*—Workman Nydegger

(57) ABSTRACT

A suture clamping system, including a plurality of elements positioned together in a row, wherein at least one of the elements is flexible, the plurality of elements each being dimensioned such that an opening slot is formed through the row of elements when the at least one flexible element is biased into a first position, and wherein a tortuous path is formed through the row of elements when the elements are not biased. A method of clamping a suture pair, including biasing a row of adjacent flexible elements to a first position in which an opening slot is formed there along; receiving the suture pair into the opening slot; and removing the biasing such that the adjacent flexible elements move to positions which hold the suture pair in a tortuous path.

20 Claims, 14 Drawing Sheets

U.S. PATENT DOCUMENTS

| | | |
|---|---|---|
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,523,351 A | 8/1970 | Filia |
| 3,586,002 A | 6/1971 | Wood |
| 3,604,425 A | 9/1971 | Le Roy |
| 3,677,243 A | 7/1972 | Nerz |
| 3,757,629 A | 9/1973 | Schneider |
| 3,805,337 A | 4/1974 | Branstetter |
| 3,828,791 A | 8/1974 | Santos |
| 3,856,016 A | 12/1974 | Davis |
| 3,908,662 A | 9/1975 | Razgulov et al. |
| 3,944,114 A | 3/1976 | Coppens |
| 4,014,492 A | 3/1977 | Rothfuss |
| 4,064,881 A | 12/1977 | Meredith |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,215,699 A | 8/1980 | Patel |
| 4,217,902 A | 8/1980 | March |
| 4,278,091 A | 7/1981 | Borzone |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,387,489 A * | 6/1983 | Dudek .................. 24/133 |
| 4,396,139 A | 8/1983 | Hall et al. |
| 4,400,879 A * | 8/1983 | Hildreth ................ 132/151 |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,485,816 A | 12/1984 | Krumme |
| RE31,855 E | 3/1985 | Osborne |
| 4,505,273 A | 3/1985 | Braun et al. |
| 4,523,695 A | 6/1985 | Braun et al. |
| 4,525,157 A | 6/1985 | Valaincourt |
| 4,526,174 A | 7/1985 | Froehlich |
| 4,586,503 A | 5/1986 | Kirsch et al. |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,665,906 A | 5/1987 | Jervis |
| 4,687,469 A | 8/1987 | Osypka |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,917,087 A | 4/1990 | Walsh et al. |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,997,439 A | 3/1991 | Chen |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,047,047 A | 9/1991 | Yoon |
| 5,053,008 A | 10/1991 | Bajaj |
| 5,061,274 A | 10/1991 | Kensey |
| 5,092,941 A | 3/1992 | Miura |
| 5,100,418 A | 3/1992 | Yoon et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,457 A | 9/1993 | Akopov et al. |
| 5,246,156 A | 9/1993 | Rothfuss et al. |
| 5,246,443 A | 9/1993 | Mai |
| 5,250,058 A | 10/1993 | Miller et al. |
| 5,269,792 A | 12/1993 | Kovac et al. |
| 5,275,616 A | 1/1994 | Fowler |
| 5,282,808 A | 2/1994 | Kovac et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,184 A | 4/1994 | Hathaway et al. |
| 5,306,254 A | 4/1994 | Nash et al. |
| 5,318,542 A | 6/1994 | Hirsch et al. |
| 5,320,639 A | 6/1994 | Rudnick |
| 5,330,442 A * | 7/1994 | Green et al. ............... 606/232 |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |

| | | | | | | |
|---|---|---|---|---|---|---|
| 5,383,896 | A | 1/1995 | Gershony et al. | 5,795,958 | A | 8/1998 | Rao et al. |
| RE34,866 | E | 2/1995 | Kensey et al. | 5,797,931 | A | 8/1998 | Bito et al. |
| 5,392,978 | A | 2/1995 | Velez | 5,797,933 | A | 8/1998 | Snow et al. |
| 5,395,030 | A | 3/1995 | Kuramoto et al. | 5,797,958 | A | 8/1998 | Yoon |
| 5,411,520 | A | 5/1995 | Nash et al. | 5,810,776 | A | 9/1998 | Bacich et al. |
| 5,413,571 | A | 5/1995 | Katsaros et al. | 5,810,846 | A | 9/1998 | Virnich et al. |
| 5,413,584 | A | 5/1995 | Schulze | 5,810,851 | A | 9/1998 | Yoon |
| 5,416,584 | A | 5/1995 | Kay | 5,817,113 | A | 10/1998 | Gifford, III et al. |
| 5,417,699 | A | 5/1995 | Klein et al. | 5,820,631 | A | 10/1998 | Nobles |
| 5,419,777 | A | 5/1995 | Hofling | 5,827,298 | A | 10/1998 | Hart et al. |
| 5,423,857 | A | 6/1995 | Rosenman et al. | 5,830,125 | A | 11/1998 | Scribner et al. |
| 5,425,489 | A | 6/1995 | Shichman et al. | 5,833,698 | A | 11/1998 | Hinchliffe et al. |
| 5,431,639 | A | 7/1995 | Shaw | 5,853,421 | A | 12/1998 | Leschinsky et al. |
| 5,431,667 | A | 7/1995 | Thompson et al. | 5,853,422 | A | 12/1998 | Huebsch et al. |
| 5,437,631 | A | 8/1995 | Janzen | 5,855,312 | A | 1/1999 | Toledano |
| 5,443,481 | A | 8/1995 | Lee | 5,858,082 | A | 1/1999 | Cruz et al. |
| 5,449,359 | A | 9/1995 | Groiso | 5,860,991 | A | 1/1999 | Klein et al. |
| 5,456,400 | A | 10/1995 | Shichman et al. | 5,861,005 | A | 1/1999 | Kontos |
| 5,462,561 | A | 10/1995 | Voda | 5,868,755 | A | 2/1999 | Kanner et al. |
| 5,470,010 | A | 11/1995 | Rothfuss et al. | 5,871,474 | A | 2/1999 | Hermann et al. |
| 5,474,557 | A | 12/1995 | Mai | 5,871,501 | A | 2/1999 | Leschinsky et al. |
| 5,478,352 | A | 12/1995 | Fowler | 5,871,525 | A | 2/1999 | Edwards et al. |
| 5,478,353 | A | 12/1995 | Yoon | 5,879,366 | A | 3/1999 | Shaw et al. |
| 5,478,354 | A | 12/1995 | Tovey et al. | 5,902,310 | A | 5/1999 | Foerster et al. |
| 5,486,195 | A | 1/1996 | Myers et al. | 5,904,697 | A | 5/1999 | Gifford, III et al. |
| 5,497,933 | A | 3/1996 | DeFonzo et al. | 5,907,893 | A | 6/1999 | Zadno-Azizi et al. |
| 5,507,744 | A | 4/1996 | Tay et al. | 5,910,155 | A | 6/1999 | Ratcliff et al. |
| 5,507,755 | A | 4/1996 | Gresl et al. | 5,922,009 | A | 7/1999 | Epstein et al. |
| 5,522,840 | A | 6/1996 | Krajicek | 5,935,147 | A | 8/1999 | Kensey et al. |
| 5,527,322 | A | 6/1996 | Klein et al. | 5,938,667 | A | 8/1999 | Peyser et al. |
| 5,536,251 | A | 7/1996 | Evard et al. | 5,941,890 | A | 8/1999 | Voegele et al. |
| 5,540,712 | A | 7/1996 | Kleshinski et al. | 5,947,999 | A | 9/1999 | Groiso |
| 5,540,716 | A | 7/1996 | Hlavacek | 5,951,518 | A | 9/1999 | Licata et al. |
| 5,544,802 | A | 8/1996 | Crainich | 5,951,576 | A | 9/1999 | Wakabayashi |
| 5,547,474 | A | 8/1996 | Kloeckl et al. | 5,951,589 | A | 9/1999 | Epstein et al. |
| 5,560,532 | A | 10/1996 | DeFonzo et al. | 5,964,782 | A | 10/1999 | Lafontaine et al. |
| 5,575,771 | A | 11/1996 | Walinsky | 5,984,934 | A | 11/1999 | Ashby et al. |
| 5,584,879 | A | 12/1996 | Reimold et al. | 5,984,949 | A | 11/1999 | Levin |
| 5,591,205 | A | 1/1997 | Fowler | 5,993,468 | A | 11/1999 | Rygaard |
| 5,593,412 | A | 1/1997 | Martinez et al. | 5,993,476 | A | 11/1999 | Groiso |
| 5,601,602 | A | 2/1997 | Fowler | 6,001,110 | A | 12/1999 | Adams |
| 5,618,291 | A | 4/1997 | Thompson et al. | 6,004,341 | A | 12/1999 | Zhu et al. |
| 5,620,452 | A | 4/1997 | Yoon | 6,007,563 | A | 12/1999 | Nash et al. |
| 5,620,461 | A | 4/1997 | Muijs Van De Moer et al. | 6,022,372 | A | 2/2000 | Kontos |
| 5,643,318 | A | 7/1997 | Tsukernik et al. | 6,024,750 | A | 2/2000 | Mastri |
| 5,645,565 | A | 7/1997 | Rudd et al. | 6,030,364 | A | 2/2000 | Durgin et al. |
| 5,645,566 | A | 7/1997 | Brenneman et al. | 6,030,413 | A | 2/2000 | Lazarus |
| 5,645,567 | A | 7/1997 | Crainich | 6,033,427 | A | 3/2000 | Lee |
| D383,539 | S | 9/1997 | Croley | 6,036,703 | A | 3/2000 | Evans et al. |
| 5,674,231 | A | 10/1997 | Green et al. | 6,036,720 | A | 3/2000 | Abrams et al. |
| 5,676,689 | A | 10/1997 | Kensey et al. | 6,045,570 | A | 4/2000 | Epstein et al. |
| 5,676,974 | A | 10/1997 | Valdes et al. | 6,048,358 | A | 4/2000 | Barak |
| 5,683,405 | A | 11/1997 | Yacoubian et al. | 6,056,768 | A | 5/2000 | Cates et al. |
| 5,690,674 | A | 11/1997 | Diaz | 6,056,769 | A | 5/2000 | Epstein et al. |
| 5,695,504 | A | 12/1997 | Gifford, III et al. | 6,056,770 | A | 5/2000 | Epstein et al. |
| 5,695,505 | A | 12/1997 | Yoon | 6,059,800 | A | 5/2000 | Hart et al. |
| 5,695,524 | A | 12/1997 | Kelley et al. | 6,063,085 | A | 5/2000 | Tay et al. |
| 5,700,273 | A | 12/1997 | Buelna et al. | 6,077,281 | A | 6/2000 | Das |
| 5,716,375 | A | 2/1998 | Fowler | 6,077,291 | A | 6/2000 | Das |
| 5,720,755 | A | 2/1998 | Dakov | 6,080,182 | A | 6/2000 | Shaw et al. |
| 5,725,554 | A | 3/1998 | Simon et al. | 6,080,183 | A | 6/2000 | Tsugita et al. |
| 5,728,114 | A | 3/1998 | Evans et al. | 6,090,130 | A | 7/2000 | Nash et al. |
| 5,728,122 | A | 3/1998 | Leschinsky et al. | 6,099,553 | A * | 8/2000 | Hart et al. .................. 606/232 |
| 5,728,132 | A | 3/1998 | Van Tassel et al. | 6,102,271 | A | 8/2000 | Longo et al. |
| 5,732,872 | A | 3/1998 | Bolduc et al. | 6,110,184 | A | 8/2000 | Weadock |
| 5,752,966 | A | 5/1998 | Chang | 6,113,612 | A | 9/2000 | Swanson et al. |
| 5,755,778 | A | 5/1998 | Kleshinski | 6,117,125 | A | 9/2000 | Rothbarth et al. |
| 5,766,246 | A | 6/1998 | Mulhauser et al. | 6,117,148 | A | 9/2000 | Ravo |
| 5,769,870 | A | 6/1998 | Salahieh et al. | 6,120,524 | A | 9/2000 | Taheri |
| 5,779,707 | A | 7/1998 | Bertholet et al. | 6,149,660 | A | 11/2000 | Laufer et al. |
| 5,782,844 | A | 7/1998 | Yoon et al. | 6,149,667 | A | 11/2000 | Hovland et al. |
| 5,782,860 | A | 7/1998 | Epstein et al. | 6,152,144 | A | 11/2000 | Lesh et al. |
| 5,782,861 | A | 7/1998 | Cragg et al. | 6,152,937 | A | 11/2000 | Peterson et al. |

| | | | | | |
|---|---|---|---|---|---|
| 6,193,734 B1 | 2/2001 | Bolduc et al. | 2001/0007077 A1 | 7/2001 | Ginn et al. |
| 6,197,042 B1 | 3/2001 | Ginn et al. | 2001/0031972 A1 | 10/2001 | Robertson et al. |
| 6,206,913 B1 | 3/2001 | Yencho et al. | 2001/0047180 A1 | 11/2001 | Grudem et al. |
| 6,220,248 B1 | 4/2001 | Voegele et al. | 2002/0026215 A1 | 2/2002 | Redmond et al. |
| 6,221,102 B1 | 4/2001 | Baker et al. | 2002/0042622 A1 | 4/2002 | Vargas et al. |
| 6,254,642 B1 | 7/2001 | Taylor | 2002/0049427 A1 | 4/2002 | Wiener et al. |
| 6,277,140 B2 | 8/2001 | Ginn et al. | 2002/0049472 A1 | 4/2002 | Coleman et al. |
| 6,280,460 B1 | 8/2001 | Bolduc et al. | 2002/0058960 A1 | 5/2002 | Hudson et al. |
| 6,287,322 B1 | 9/2001 | Zhu et al. | 2002/0072768 A1 | 6/2002 | Ginn |
| 6,305,891 B1 | 10/2001 | Burlingame | 2002/0077657 A1 | 6/2002 | Ginn et al. |
| 6,322,580 B1 | 11/2001 | Kanner | 2002/0082641 A1 | 6/2002 | Ginn et al. |
| 6,334,865 B1 | 1/2002 | Redmond et al. | 2002/0107542 A1 | 8/2002 | Kanner et al. |
| 6,348,064 B1 | 2/2002 | Kanner | 2002/0133193 A1 | 9/2002 | Ginn et al. |
| D457,958 S | 5/2002 | Dycus | 2002/0151921 A1 | 10/2002 | Kanner et al. |
| 6,383,208 B1 | 5/2002 | Sancoff et al. | 2002/0193808 A1 | 12/2002 | Belef et al. |
| 6,391,048 B1 | 5/2002 | Ginn et al. | 2003/0004543 A1 | 1/2003 | Gleeson et al. |
| 6,398,752 B1 | 6/2002 | Sweezer et al. | 2003/0009180 A1 | 1/2003 | Hinchliffe et al. |
| 6,402,765 B1 | 6/2002 | Monassevitch et al. | 2003/0032981 A1 | 2/2003 | Kanner et al. |
| 6,409,739 B1 | 6/2002 | Nobles et al. | 2003/0065358 A1 | 4/2003 | Frecker et al. |
| 6,419,669 B1 | 7/2002 | Frazier et al. | 2003/0078598 A1 | 4/2003 | Ginn et al. |
| 6,428,548 B1 | 8/2002 | Durgin et al. | 2003/0083679 A1 | 5/2003 | Grudem et al. |
| 6,443,158 B1 | 9/2002 | Lafontaine et al. | 2003/0093096 A1 | 5/2003 | McGuckin et al. |
| 6,450,391 B1 | 9/2002 | Kayan et al. | 2003/0097140 A1 | 5/2003 | Kanner |
| 6,458,130 B1 | 10/2002 | Frazier et al. | 2003/0109890 A1 | 6/2003 | Kanner et al. |
| 6,461,364 B1 | 10/2002 | Ginn et al. | 2003/0125766 A1 | 7/2003 | Ding |
| 6,488,692 B1 | 12/2002 | Spence et al. | 2003/0158577 A1 | 8/2003 | Pantages et al. |
| 6,500,115 B2 | 12/2002 | Krattiger et al. | 2003/0158578 A1 | 8/2003 | Pantages et al. |
| 6,506,210 B1 | 1/2003 | Kanner | 2003/0195504 A1 | 10/2003 | Tallarida et al. |
| 6,517,569 B2 | 2/2003 | Mikus et al. | 2003/0195561 A1 | 10/2003 | Carley et al. |
| 6,533,762 B2 | 3/2003 | Kanner et al. | 2004/0009289 A1 | 1/2004 | Carley et al. |
| 6,537,288 B2 | 3/2003 | Vargas et al. | 2004/0010285 A1 | 1/2004 | Carley et al. |
| 6,547,806 B1 | 4/2003 | Ding | 2004/0039414 A1 | 2/2004 | Carley et al. |
| 6,569,173 B1 | 5/2003 | Blatter et al. | 2004/0073236 A1 | 4/2004 | Carley et al. |
| 6,582,452 B2 | 6/2003 | Coleman et al. | 2004/0073255 A1 | 4/2004 | Ginn et al. |
| 6,599,303 B1 | 7/2003 | Peterson et al. | 2004/0082906 A1 | 4/2004 | Tallarida et al. |
| 6,602,263 B1 | 8/2003 | Swanson et al. | 2004/0087985 A1 | 5/2004 | Loshakove et al. |
| 6,616,686 B2 | 9/2003 | Coleman et al. | 2004/0092968 A1 | 5/2004 | Caro et al. |
| 6,623,510 B2 | 9/2003 | Carley et al. | 2004/0153122 A1 | 8/2004 | Palermo |
| 6,626,918 B1 | 9/2003 | Ginn et al. | 2004/0153123 A1 | 8/2004 | Palermo et al. |
| 6,632,238 B2 | 10/2003 | Ginn et al. | 2004/0167570 A1 | 8/2004 | Pantages |
| 6,634,537 B2 | 10/2003 | Chen | 2004/0254591 A1 | 12/2004 | Kanner et al. |
| 6,645,205 B2 | 11/2003 | Ginn | 2004/0267312 A1 | 12/2004 | Kanner et al. |
| 6,652,538 B2 | 11/2003 | Kayan et al. | 2005/0090859 A1 | 4/2005 | Ravlkumar |
| 6,669,714 B2 | 12/2003 | Coleman et al. | 2005/0119695 A1 | 6/2005 | Carley et al. |
| 6,676,671 B2 | 1/2004 | Robertson et al. | 2005/0165357 A1 | 7/2005 | McGuckin et al. |
| 6,679,904 B2 | 1/2004 | Gleeson et al. | 2005/0216057 A1 | 9/2005 | Coleman et al. |
| 6,695,867 B2 | 2/2004 | Ginn et al. | 2005/0234508 A1 | 10/2005 | Cummins et al. |
| 6,699,256 B1 | 3/2004 | Logan et al. | 2005/0267530 A1 | 12/2005 | Cummins et al. |
| 6,702,826 B2 | 3/2004 | Liddicoat et al. | 2005/0273136 A1 | 12/2005 | Belef et al. |
| 6,712,836 B1 | 3/2004 | Berg et al. | 2005/0274768 A1 | 12/2005 | Cummins et al. |
| 6,719,777 B2 | 4/2004 | Ginn et al. | 2005/0283188 A1 | 12/2005 | Loshakove et al. |
| 6,726,704 B1 | 4/2004 | Loshakove et al. | 2006/0020270 A1 | 1/2006 | Jabba et al. |
| 6,749,621 B2 | 6/2004 | Pantages et al. | 2006/0135989 A1 | 6/2006 | Carley et al. |
| 6,749,622 B2 | 6/2004 | McGuckin et al. | 2006/0144479 A1 | 7/2006 | Carley et al. |
| 6,755,842 B2 | 6/2004 | Kanner et al. | 2006/0167484 A1 | 7/2006 | Carley et al. |
| 6,767,356 B2 | 7/2004 | Kanner et al. | 2006/0190014 A1 | 8/2006 | Ginn et al. |
| 6,780,197 B2 | 8/2004 | Roe et al. | 2006/0190038 A1 | 8/2006 | Carley et al. |
| 6,846,319 B2 | 1/2005 | Ginn et al. | 2006/0195123 A1 | 8/2006 | Ginn et al. |
| 6,896,687 B2 | 5/2005 | Dakov | 2006/0195124 A1 | 8/2006 | Ginn et al. |
| 6,926,723 B1 | 8/2005 | Mulhauser et al. | 2006/0287674 A1 | 12/2006 | Ginn et al. |
| 6,926,731 B2 | 8/2005 | Coleman et al. | 2007/0010853 A1 | 1/2007 | Ginn et al. |
| 6,942,674 B2 | 9/2005 | Belef et al. | 2007/0010854 A1 | 1/2007 | Cummins et al. |
| 6,989,003 B2 | 1/2006 | Wing et al. | 2007/0270904 A1 | 11/2007 | Ginn |
| 6,989,016 B2 | 1/2006 | Tallarida et al. | 2007/0276416 A1 | 11/2007 | Ginn et al. |
| 7,001,398 B2 | 2/2006 | Carley et al. | 2007/0282352 A1 | 12/2007 | Carley et al. |
| 7,108,709 B2 | 9/2006 | Cummins | 2008/0004636 A1 | 1/2008 | Walberg |
| 7,111,768 B2 | 9/2006 | Cummins et al. | 2008/0065152 A1 | 3/2008 | Carley |
| 7,144,411 B2 | 12/2006 | Ginn et al. | 2008/0210737 A1 | 9/2008 | Ginn et al. |
| 7,163,551 B2 | 1/2007 | Anthony et al. | 2008/0221616 A1 | 9/2008 | Ginn et al. |
| 7,169,158 B2 | 1/2007 | Sniffin et al. | 2008/0269801 A1 | 10/2008 | Coleman et al. |
| 7,211,101 B2 | 5/2007 | Carley et al. | 2008/0269802 A1 | 10/2008 | Coleman et al. |
| D566,272 S | 4/2008 | Walberg et al. | 2008/0272173 A1 | 11/2008 | Coleman et al. |
| 7,396,359 B1 | 7/2008 | Derowe et al. | 2008/0312666 A1 | 12/2008 | Ellingwood et al. |

2008/0312686 A1  12/2008  Ellingwood

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 715 290 | 7/1995 |
| FR | 2 722 975 | 2/1996 |
| GB | 1 358 466 | 7/1974 |
| GB | 2 075 144 | 11/1981 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 12 74750 | 11/1989 |
| JP | 11500642 | 8/1997 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07640 | 2/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/45593 | 6/2002 |
| WO | WO 02/45594 | 6/2002 |
| WO | WO 02/98302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/101310 | 12/2003 |
| WO | WO 2004/004578 | 1/2004 |
| WO | WO 2004/060169 | 7/2004 |
| WO | WO 2004/069054 | 8/2004 |
| WO | WO 2005/082256 | 9/2005 |
| WO | WO 2005/115521 | 12/2005 |
| WO | WO 2006/083889 | 8/2006 |
| WO | WO 2007/005585 | 1/2007 |
| WO | WO 2008/031102 | 3/2008 |
| ZA | 200100527 | 1/2001 |

OTHER PUBLICATIONS

U.S. Appl. No. 60/946,026, filed Jun. 25, 2007, Ellingwood.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
U.S. Appl. No. 09/680,837, Mail Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Action.
U.S. Appl. No. 09/680,837, Mail Date Jun. 16, 2003, Notice Of Allowance.
U.S. Appl. No. 09/680,837, Mail Date Sep. 11, 2003, Issue Notification.
U.S. Appl. No. 10/006,400, Mail Date Jan. 2, 2009, Office Action.
U.S. Appl. No. 10/147,774, Mail Date Mar. 18, 2009, Office Action.
U.S. Appl. No. 10/264,306, Mail Date Feb. 26, 2009, Office Action.
U.S. Appl. No. 10/356,214, Mail Date Nov. 4, 2008, Office Action.
U.S. Appl. No. 10/356,214, Mail Date Apr. 29, 2009, Office Action.
U.S. Appl. No. 10/435,104, Mail Date Nov. 14, 2007, Notice Of Allowance.
U.S. Appl. No. 10/435,104, Mail Date Dec. 22, 2008, Notice Of Allowance.
U.S. Appl. No. 10/517,004, Mail Date Aug. 13, 2008, Notice Of Allowance.
U.S. Appl. No. 10/517,004, Mail Date Feb. 10, 2009, Notice Of Allowance.
U.S. Appl. No. 10/541,083, Mail Date Oct. 31, 2007, Office Action.
U.S. Appl. No. 10/541,083, Mail Date Dec. 29, 2008, Notice Of Allowance.
U.S. Appl. No. 10/638,115, Mail Date Oct. 29, 2008, Office Action.
U.S. Appl. No. 10/667,144, Mail Date Mar. 24, 2009, Office Action.
U.S. Appl. No. 10/669,313, Mail Date Oct. 31, 2005, Office Action.
U.S. Appl. No. 10/669,313, Mail Date Jan. 11, 2006, Notice Of Allowance.
U.S. Appl. No. 10/669,313, Mail Date Jun. 28, 2006, Notice Of Allowance.
U.S. Appl. No. 10/669,313, Mail Date Nov. 15, 2006, Issue Notification.
U.S. Appl. No. 10/682,459, Mail Date Dec. 4, 2008, Office Action.
U.S. Appl. No. 10/787,073, Mail Date Nov. 12, 2008, Office Action.
U.S. Appl. No. 10/908,721, Mail Date Nov. 25, 2008, Office Action.
U.S. Appl. No. 11/048,503, Mail Date Mar. 13, 2009, Office Action.
U.S. Appl. No. 11/152,562, Mail Date Feb. 13, 2009, Office Action.
U.S. Appl. No. 11/344,793, Mail Date Jan. 22, 2009, Office Action.
U.S. Appl. No. 11/344,868, Mail Date Mar. 25, 2009, Office Action.
U.S. Appl. No. 11/344,891, Mail Date Dec. 8, 2008, Office Action.
U.S. Appl. No. 11/344,891, Mail Date Feb. 26, 2009, Office Action.
U.S. Appl. No. 11/396,731, Mail Date Feb. 13, 2009, Office Action.

U.S. Appl. No. 11/406,203, Mail Date Mar. 3, 2009, Office Action.
U.S. Appl. No. 11/427,297, Mail Date Jan. 30, 2009, Office Action.
U.S. Appl. No. 11/532,325, Mail Date Feb. 23, 2009, Office Action.
U.S. Appl. No. 11/744,089, Mail Date Nov. 26, 2008, Office Action.
U.S. Appl. No. 12/106,928, Mail Date Jan. 23, 2009, Office Action.
U.S. Appl. No. 12/106,937, Mail Date Mar. 30, 2009, Office Action.
U.S. Appl. No. 29/296,370, Mail Date Aug. 18, 2008, Office Action.
U.S. Appl. No. 29/296,370, Mail Date Dec. 2, 2008, Notice Of Allowance.
U.S. Appl. No. 29,296,370, Mail Date Apr. 1, 2009, Notice Of Allowance.
U.S. Appl. No. 09/478,179, Mail Date Nov. 6, 2000, Notice of Allowance.
U.S. Appl. No. 09/478,179, Mail Date Feb. 15, 2001, Issue Notification.
U.S. Appl. No. 09/546,998, Mail Date May 6, 2002, Notice of Allowance.
U.S. Appl. No. 09/546,998, Mail Date Sep. 19, 2002, Issue Notification.
U.S. Appl. No. 09/610,238, Mail Date Mar. 26, 2001, Notice of Allowance.
U.S. Appl. No. 09/610,238, Mail Date Sep. 5, 2001, Office Action.
U.S. Appl. No. 09/610,238, Mail Date Feb. 11, 2002, Notice of Allowance.
U.S. Appl. No. 09/610,238, Mail Date May 3, 2002, Issue Notification.
U.S. Appl. No. 09/732,178, Mail Date Aug. 1, 2002, Office Action.
U.S. Appl. No. 09/732,178, Mail Date Dec. 24, 2002, Office Action.
U.S. Appl. No. 09/732,178, Mail Date Jun. 10, 2003, Office Action.
U.S. Appl. No. 09/732,178, Mail Date Jul. 3, 2003, Office Action.
U.S. Appl. No. 09/732,178, Mail Date Nov. 17, 2003, Notice of Allowance.
U.S. Appl. No. 09/732,178, Mail Date Mar. 25, 2004, Issue Notification.
U.S. Appl. No. 09/732,835, Mail Date Sep. 11, 2003, Office Action.
U.S. Appl. No. 09/732,835, Mail Date Feb. 9, 2004, Office Action.
U.S. Appl. No. 09/732,835, Mail Date Mar. 17, 2004, Notice of Allowance.
U.S. Appl. No. 09/764,813, Mail Date Mar. 26, 2001, Office Action.
U.S. Appl. No. 09/764,813, Mail Date Jun. 4, 2001, Notice of Allowance.
U.S. Appl. No. 09/764,813, Mail Date Aug. 6, 2001, Issue Notification.
U.S. Appl. No. 09/933,299, Mail Date Feb. 26, 2003, Office Action.
U.S. Appl. No. 09/933,299, Mail Date Jun. 16, 2003, Notice of Allowance.
U.S. Appl. No. 09/933,299, Mail Date Sep. 25, 2003, Issue Notification.
U.S. Appl. No. 09/948,813, Mail Date Jan. 31, 2003, Notice of Allowance.
U.S. Appl. No. 09/948,813, Mail Date Jun. 5, 2003, Issue Notification.
U.S. Appl. No. 09/949,398, Mail Date Mar. 4, 2003, Office Action.
U.S. Appl. No. 09/949,398, Mail Date Jul. 28, 2003, Notice of Allowance.
U.S. Appl. No. 09/949,398, Mail Date Dec. 11, 2003, Issue Notification.
U.S. Appl. No. 09/949,438, Mail Date Dec. 17, 2002, Office Action.
U.S. Appl. No. 09/949,438, Mail Date Apr. 21, 2003, Notice of Allowance.
U.S. Appl. No. 09/949,438, Mail Date Aug. 21, 2003, Issue Notification.
U.S. Appl. No. 10/006,400, Mail Date Aug. 27, 2004, Office Action.
U.S. Appl. No. 10/006,400, Mail Date Feb. 23, 2005, Office Action.
U.S. Appl. No. 10/006,400, Mail Date Apr. 11, 2005, Office Action.
U.S. Appl. No. 10/006,400, Mail Date Jul. 27, 2005, Office Action.
U.S. Appl. No. 10/006,400, Mail Date Mar. 6, 2006, Office Action.
U.S. Appl. No. 10/006,400, Mail Date May 24, 2006, Office Action.
U.S. Appl. No. 10/006,400, Mail Date Oct. 26, 2006, Office Action.
U.S. Appl. No. 10/006,400, Mail Date Apr. 19, 2007, Office Action.
U.S. Appl. No. 10/006,400, Mail Date Apr. 2, 2008, Office Action.
U.S. Appl. No. 10/081,717, Mail Date Sep. 29, 2003, Notice of Allowance.
U.S. Appl. No. 10/081,717, Mail Date Feb. 5, 2004, Issue Notification.
U.S. Appl. No. 10/081,723, Mail Date Sep. 29, 2004, Office Action.
U.S. Appl. No. 10/081,723, Mail Date May 13, 2005, Notice of Allowance.
U.S. Appl. No. 10/081,725, Mail Date Feb. 9, 2004, Notice of Allowance.
U.S. Appl. No. 10/081,725, Mail Date Apr. 13, 2004, Office Action.
U.S. Appl. No. 10/081,725, Mail Date May 27, 2004, Issue Notification.
U.S. Appl. No. 10/081,726, Mail Date Apr. 11, 2003, Notice of Allowance.
U.S. Appl. No. 10/081,726, Mail Date Jun. 9, 2003, Office Action.
U.S. Appl. No. 10/081,726, Mail Date Sep. 4, 2003, Issue Notification.
U.S. Appl. No. 10/147,774, Mail Date Nov. 4, 2004, Office Action.
U.S. Appl. No. 10/147,774, Mail Date May 4, 2004, Office Action.
U.S. Appl. No. 10/147,774, Mail Date Oct. 18, 2005, Office Action.
U.S. Appl. No. 10/147,774, Mail Date Apr. 18, 2007, Notice of Allowance.
U.S. Appl. No. 10/147,774, Mail Date Sep. 27, 2007, Notice of Allowance.
U.S. Appl. No. 10/147,774, Mail Date Feb. 4, 2004, Notice of Allowance.
U.S. Appl. No. 10/147,774, Mail Date Jun. 30, 2008, Office Action.
U.S. Appl. No. 10/240,183, Mail Date Jul. 27, 2004, Office Action.
U.S. Appl. No. 10/240,183, Mail Date Dec. 17, 2004, Office Action.
U.S. Appl. No. 10/240,183, Mail Date Mar. 9, 2005, Notice of Allowance.
U.S. Appl. No. 10/240,183, Mail Date Aug. 11, 2006, Office Action.
U.S. Appl. No. 10/264,306, Mail Date Feb. 9, 2005, Office Action.
U.S. Appl. No. 10/264,306, Mail Date May 26, 2005, Office Action.
U.S. Appl. No. 10/264,306, Mail Date Oct. 4, 2005, Office Action.
U.S. Appl. No. 10/264,306, Mail Date May 10, 2006, Notice of Allowance.
U.S. Appl. No. 10/264,306, Mail Date Jul. 2, 2007, Notice of Allowance.
U.S. Appl. No. 10/264,306, Mail Date Feb. 4, 2008, Notice of Allowance.
U.S. Appl. No. 10/264,306, Mail Date Jun. 27, 2008, Office Action.
U.S. Appl. No. 10/335,075, Mail Date Aug. 10, 2005, Office Action.
U.S. Appl. No. 10/335,075, Mail Date Dec. 19, 2005, Office Action.
U.S. Appl. No. 10/335,075, Mail Date Apr. 21, 2006, Office Action.
U.S. Appl. No. 10/335,075, Mail Date Dec. 27, 2006, Notice of Allowance.
U.S. Appl. No. 10/335,075, Mail Date Apr. 11, 2007, Issue Notification.
U.S. Appl. No. 10/356,214, Mail Date Nov. 30, 2005, Office Action.
U.S. Appl. No. 10/356,214, Mail Date Aug. 23, 2006, Office Action.
U.S. Appl. No. 10/356,214, Mail Date Feb. 13, 2007, Office Action.
U.S. Appl. No. 10/356,214, Mail Date Sep. 12, 2007, Office Action.
U.S. Appl. No. 10/356,214, Mail Date Mar. 6, 2008, Office Action.
U.S. Appl. No. 10/435,104, Mail Date Jun. 10, 2004, Office Action.
U.S. Appl. No. 10/435,104, Mail Date Sep. 21, 2004, Notice of Allowance.
U.S. Appl. No. 10/435,104, Mail Date Jan. 3, 2006, Office Action.
U.S. Appl. No. 10/435,104, Mail Date Feb. 15, 2006, Issue Notification.
U.S. Appl. No. 10/435,104, Mail Date May 16, 2006, Office Action.
U.S. Appl. No. 10/435,104, Mail Date Dec. 28, 2006, Notice of Allowance.
U.S. Appl. No. 10/435,104, Mail Date May 23, 2007, Issue Notification.
U.S. Appl. No. 10/435,104, Mail Date Jul. 10, 2007, Notice of Allowance.
U.S. Appl. No. 10/435,104, Mail Date Aug. 2, 2007, Notice of Allowance.
U.S. Appl. No. 10/435,104, Mail Date Oct. 26, 2007, Notice of Allowance.
U.S. Appl. No. 10/435,104, Mail Date Apr. 4, 2008, Notice of Allowance.
U.S. Appl. No. 10/435,104, Mail Date Sep. 26, 2008, Notice of Allowance.

U.S. Appl. No. 10/455,768, Mail Date Nov. 16, 2004, Office Action.
U.S. Appl. No. 10/455,768, Mail Date Apr. 6, 2005, Notice of Allowance.
U.S. Appl. No. 10/486,067, Mail Date Jan. 10, 2006, Office Action.
U.S. Appl. No. 10/486,067, Mail Date Sep. 20, 2006, Notice of Allowance.
U.S. Appl. No. 10/486,067, Mail Date Dec. 27, 2006, Issue Notification.
U.S. Appl. No. 10/486,070, Mail Date Apr. 20, 2005, Office Action.
U.S. Appl. No. 10/486,070, Mail Date Aug. 10, 2005, Office Action.
U.S. Appl. No. 10/486,070, Mail Date Oct. 18, 2005, Notice of Allowance.
U.S. Appl. No. 10/517,004, Mail Date Aug. 13, 2007, Office Action.
U.S. Appl. No. 10/517,004, Mail Date Jan. 30, 2008, Office Action.
U.S. Appl. No. 10/519,778, Mail Date Feb. 23, 2006, Office Action.
U.S. Appl. No. 10/519,778, Mail Date May 31, 2006, Notice of Allowance.
U.S. Appl. No. 10/541,083, Mail Date Oct. 16, 2007, Office Action.
U.S. Appl. No. 10/541,083, Mail Date May 5, 2008, Office Action.
U.S. Appl. No. 10/541,083, Mail Date Sep. 19, 2008, Notice of Allowance.
U.S. Appl. No. 10/616,832, Mail Date Jun. 30, 2006, Office Action.
U.S. Appl. No. 10/616,832, Mail Date Oct. 20, 2006, Office Action.
U.S. Appl. No. 10/616,832, Mail Date May 29, 2007, Office Action.
U.S. Appl. No. 10/616,832, Mail Date Jan. 22, 2008, Office Action.
U.S. Appl. No. 10/616,832, Mail Date Sep. 17, 2008, Office Action.
U.S. Appl. No. 10/617,090, Mail Date Mar. 22, 2005, Office Action.
U.S. Appl. No. 10/617,090, Mail Date Jul. 6, 2005, Notice of Allowance.
U.S. Appl. No. 10/617,090, Mail Date Oct. 5, 2005, Notice of Allowance.
U.S. Appl. No. 10/617,090, Mail Date Feb. 1, 2006, Issue Notification.
U.S. Appl. No. 10/638,115, Mail Date Sep. 22, 2006, Office Action.
U.S. Appl. No. 10/638,115, Mail Date Jan. 31, 2007, Office Action.
U.S. Appl. No. 10/638,115, Mail Date Sep. 18, 2007, Office Action.
U.S. Appl. No. 10/638,115, Mail Date Feb. 7, 2008, Office Action.
U.S. Appl. No. 10/638,115, Mail Date May 7, 2009, Notice of Allowance.
U.S. Appl. No. 10/667,144, Mail Date Sep. 19, 2006, Office Action.
U.S. Appl. No. 10/667,144, Mail Date May 2, 2007, Office Action.
U.S. Appl. No. 10/667,144, Mail Date Nov. 19, 2007, Office Action.
U.S. Appl. No. 10/667,144, Mail Date Dec. 5, 2007, Office Action.
U.S. Appl. No. 10/667,144, Mail Date May 12, 2008, Office Action.
U.S. Appl. No. 10/682,459, Mail Date Sep. 15, 2006, Office Action.
U.S. Appl. No. 10/682,459, Mail Date Apr. 18, 2007, Office Action.
U.S. Appl. No. 10/682,459, Mail Date Apr. 2, 2008, Office Action.
U.S. Appl. No. 10/786,444, Mail Date Oct. 30, 2006, Office Action.
U.S. Appl. No. 10/786,444, Mail Date Apr. 17, 2007, Office Action.
U.S. Appl. No. 10/786,444, Mail Date Aug. 31, 2007, Office Action.
U.S. Appl. No. 10/786,444, Mail Date Apr. 24, 2008, Office Action.
U.S. Appl. No. 10/786,444, Mail Date Oct. 17, 2008, Office Action.
U.S. Appl. No. 10/787,073, Mail Date Nov. 30, 2006, Office Action.
U.S. Appl. No. 10/787,073, Mail Date Sep. 5, 2007, Office Action.
U.S. Appl. No. 10/787,073, Mail Date Feb. 22, 2008, Office Action.
U.S. Appl. No. 10/908,721, Mail Date Oct. 19, 2006, Office Action.
U.S. Appl. No. 10/908,721, Mail Date Aug. 10, 2007, Office Action.
U.S. Appl. No. 10/908,721, Mail Date Jan. 25, 2008, Office Action.
U.S. Appl. No. 11/113,549, Mail Date Feb. 6, 2007, Office Action.
U.S. Appl. No. 11/113,549, Mail Date May 30, 2007, Office Action.
U.S. Appl. No. 11/113,549, Mail Date Nov. 9, 2007, Office Action.
U.S. Appl. No. 11,113,549, Mail Date Apr. 16, 2008, Office Action.
U.S. Appl. No. 11/152,562, Mail Date May 13, 2008, Office Action.
U.S. Appl. No. 11/198,811, Mail Date Aug. 26, 2008, Office Action.
U.S. Appl. No. 11/198,811, Mail Date Apr. 6, 2009, Office Action.
U.S. Appl. No. 11/344,891, Mail Date Apr. 29, 2008, Office Action.
U.S. Appl. No. 11/396,141, Mail Date May 22, 2009, Office Action.
U.S. Appl. No. 11/396,731, Mail Date May 22, 2009, Office Action.
U.S. Appl. No. 11/406,203, Mail Date May 14, 2007, Office Action.
U.S. Appl. No. 11/406,203, Mail Date Jan. 29, 2008, Notice of Allowance.
U.S. Appl. No. 11/406,203, Mail Date May 23, 2008, Notice of Allowance.
U.S. Appl. No. 11/406,203, Mail Date Sep. 22, 2008, Notice of Allowance.
U.S. Appl. No. 11/411,925, Mail Date Jun. 6, 2007, Office Action.
U.S. Appl. No. 11/411,925, Mail Date Feb. 5, 2008, Office Action.
U.S. Appl. No. 11/411,925, Mail Date Jan. 12, 2009, Office Action.
JP2003-570704, Mail Date Jan. 13, 2009, Japanese Office Action.
U.S. Appl. No. 60/843,325, Sep. 8, 2006, Carly.
U.S. Appl. No. 60/946,030, Jun. 25, 2007, Voss et al.
U.S. Appl. No. 60,946,042, Jun. 25, 2007, Ellingwood et al.
U.S. Appl. No. 12/113,092, Apr. 30, 2008, Ginn et al.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62-No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77-No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6-No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72-No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5-No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42-No. 3, Division of Neurosurgery, University of Alberta, Edmonton, Canada.
Jeremy L Gilbert PhD, Wound Closure Biomaterials and Devices, Shock., Mar. 1999, p. 226, vol. 11-No. 3, Institution Northwestern University.
Jochen T. Cremer, MD, et al, Different approaches for minimally invasive closure of atrial septal defects, Ann. Thorac. Surg., Nov. 1998, pp. 1648-1652, Vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27-No. 6, Department of Surgery, Mercy Hospital of Pittsburgh, PA.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6-No. 5, Orlando Regional Medical Center, FL.
Michael Gianturco, A Play on Catheterization, Forbes, Dec. 1996, p. 146, vol. 158-No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183-No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63-No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45-No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19-No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83-No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.-No. 2, Supplement 1.

Stretch Comb by Scunci, retrieved via internet at www.scunci.com/productdetail by examiner on Oct. 9, 2007, publication date unavailable.

Swee Lian Tan, MD, PHD, FACS, Explanation of Infected Hemostatic Puncture Closure Devices—A Case Report, Vascular and Endovascular Surgery, 1999, pp. 507-510, vol. 33-No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9-No. 5, Department of Surgery/Urology, University of Wisconsin Medical School, Madison.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42-No. 3, Institution Department of Plastic and Reconstructive Surgery, Albert Einstein College of Medicine and Montefiore Medical Center, Bronx, NY.

Tomoaki Hinohara, Percutaneous, vascular surgery (Prostar® Plus and Techstar® for femoral artery site closure), Interventional Cardiology Newsletter, May-Jul. 1997, pp. 19-28, vol. 5-No. 3-4.

UT Aker et al, Immediate arterial hemostatis after cardiac catheterization: initial experience with a new puncture closure device, Cathet Cardiovasc Diagn, Mar. 1994, pp. 228-232, vol. 33-No. 3, Missouri Baptist Medical Center, St. Louis.

Wei Qu et al. An absorbable pinned-ring device for microvascular anastomosis of vein grafts: Experimental studies, Microsurgery 1999, Mar. 1999, pp. 128-134, vol. 19-No. 3, Department of Orthopaedic Surgery, Hiroshima University School of Medicine, Hiroshima, Japan.

William G. Kussmaul III MD, et al., Rapid arterial hemostatis and decreased access site complications after cardiac catheterization and angioplasty: Results of a randomized trial of a novel hemostatic device, Journal of the American College of Cardiology, Jun. 1995, pp. 1685-1692, vol. 25-No. 7.

* cited by examiner

MULTI-ELEMENT BIASED SUTURE CLIP

CROSS-REFERENCE TO RELATED APPLICATIONS

This is a continuation application of U.S. patent application Ser. No. 10/305,923, filed Nov. 26, 2002, now U.S. Pat. No. 7,108,710 and entitled "Multi element Biased Suture Clip", the disclosure of which is incorporated herein by this reference.

BACKGROUND OF THE INVENTION

1. The Field of the Invention

The present invention relates to systems for securing a pair of suture lengths together or for using a single strand of suture to secure tissues together at an operative site in a patient without necessarily tying a knot.

2. The Relevant Technology

Sutures are used to sew tissue together, and thereby close tissue openings, cuts or incisions during or after any of a very wide variety of medical procedures. Typically, the surgeon manually ties together a suture pair to close the opening, however, automatic suture tying systems have also been developed.

There are a number of disadvantages of knotting sutures together to secure tissues to one another. For example, manual knot tying requires considerable dexterity. Also, manual knot tying can take considerable time. Knot tying is further complicated by the fact that surgical sutures have low friction surfaces. Therefore, it is typically necessary for a surgeon to include many "throws" when tying the knot. This multiple-throw problem occurs even if an automatic knot tying device is used. Unfortunately, as the number of loops or "throws" incorporated into the knot increase, the knot becomes increasingly large and bulky. Moreover, the surgeon typically needs to handle strands of adequate suture length prior to commencing manual knot tying. Thus, manual knot tying requires considerable space both in which to view, and to perform, the actual suture knot tying. Therefore, knot tying is particularly difficult in areas of limited available space or access, such as, for example, at the back of the patient's heart during a coronary artery bypass graft (CABG) operation, or at the artery in the tissue tract after a femoral artery catheterization procedure. Manually tied knots often lock prior to reaching the intended amount of tension to be applied to the tissue. Furthermore, tissues are typically secured together by a pair of sutures wherein each of the sutures in the pair pass through both of the tissues which are then secured together by tying off the suture pair. It would instead be advantageous to provide a system which is adapted to secure tissue with suture, but without necessarily tying a knot.

BRIEF SUMMARY OF THE INVENTION

Embodiments of the present invention provide a suture clamping system. The present suture clamping system can be used to clamp a suture pair, or to use a single strand of suture to secure tissues together. In one embodiment, a plurality of elements define a slot sized to accept a suture element through the row of elements when at least one of the elements is in a first position, and wherein a tortuous path is formed through the row of elements when at least one of the elements is in a second position.

In various embodiments, the slot is generally parallel to the length of the row. In various embodiments, the at least one of the elements is a flexible element which is in the second position when not biased, and which moves into the first position when biased. In various embodiments, the direction in which the flexible element is biased is generally transverse to the length of the row.

In various embodiments, the present invention comprises a plurality of adjacent flexible elements connected together in a row. The elements are biased to first positions which define an opening slot along the row of elements. A tortuous path is formed through the elements when the elements are not biased.

Still other embodiments may also include a biasing/positioning device which is used to bias and hold the row of elements in the first position (at which time an opening is defined along the top of the row for receipt of the suture length or suture pair therein). Preferably, the biasing device is slidably received around the row of elements such that as the biasing force is removed, (e.g.: as the row of elements are slidably pushed or otherwise advanced through the biasing device), the elements then move to a non-biased position (at which time a tortuous path is formed along through the row of elements). Thus, a suture pair can effectively be clamped or "fastened" together when the sutures are held in such a tortuous path. Features of the present invention allow a physician to completely avoid manual suture knot tying. Therefore, the bulky multiple loops or "throws" required when knot tying can be minimized or eliminated. Instead, the suture pair is simply "clamped" or held together between the flexible elements.

Alternatively, the present system can be clamped onto a single suture and can thus act as an anchor preventing movement of a tissue layer along a single suture strand. Specifically, when using only a single strand of suture, the suture is clamped so that it does not move with respect to the clamping system.

DETAILED DESCRIPTION

In accordance with the present invention, a suture clamping system is provided. In preferred aspects, the suture clamping system comprises a plurality of individual flexible elements positioned together in a row. In various preferred embodiments, the individual flexible elements are shaped the same. Optionally, the row of elements is formed by positioning successive identically shaped elements adjacent to one another. It is to be understood, however, that the individual elements in the row need not be identical in shape to one another. It is also to be understood that the individual elements need not be positioned in direct "touching" contact side-by-side with one another, but may instead be positioned some distance apart from one another. As will also be explained, various embodiments of the invention may include rows of elements including both flexible and non-flexible elements. In fact, in one embodiment, only one flexible element is required.

One or more of these elements are preferably biased in a direction transverse to the length of the row. When biased, one or more flexible elements move to a first position at which the elements define a slot along the length of the row. The slot is specifically sized to receive a suture therein. When not biased, the one or more flexible elements return to a second (non-biased) position. When in a non-biased position, the elements form a tortuous path for the suture received therein.

Figure 5:
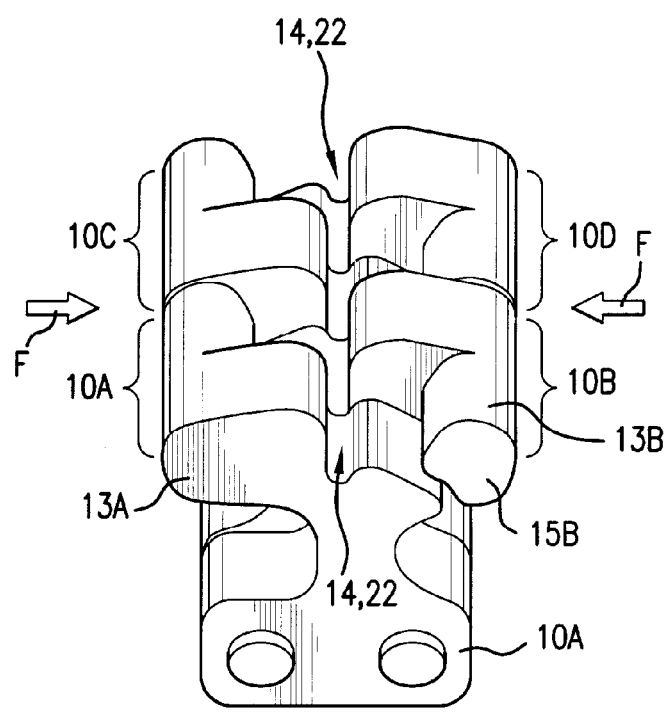
FIG. 5 is a perspective end view of the row of flexible elements as illustrated in FIG. 4.
Figure 6:
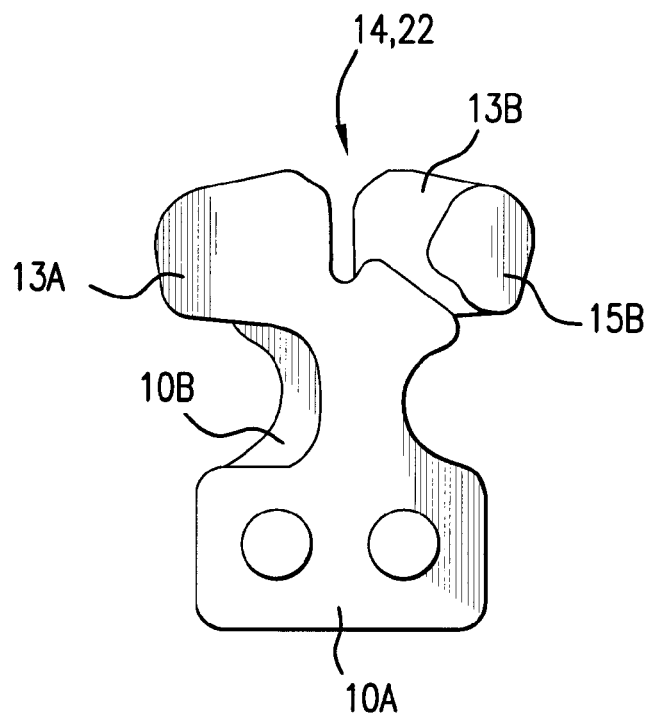
FIG. 6 is an end elevation view of the row of flexible elements as illustrated in FIGS. 4 and 5.
Figure 7:
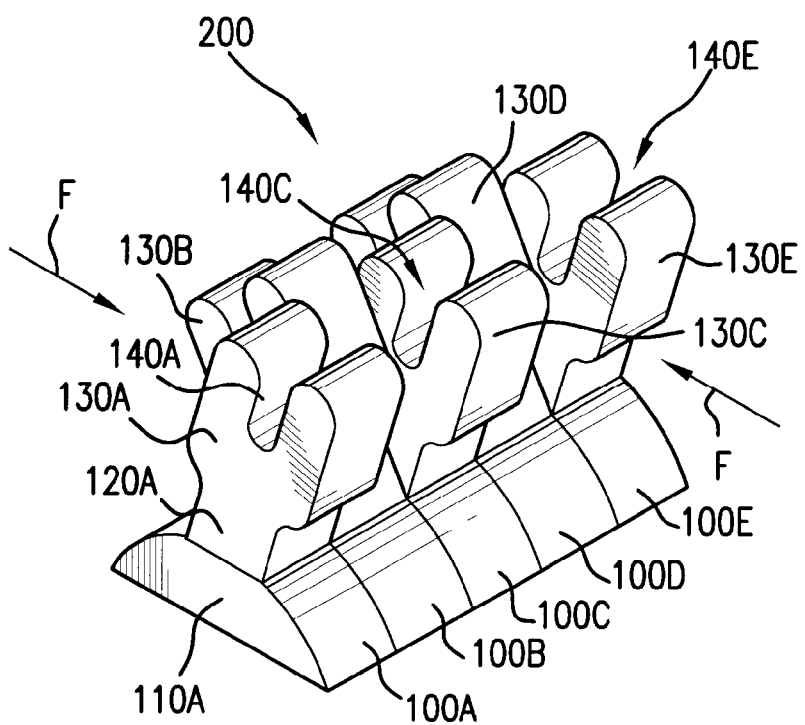
FIG. 7 is a perspective view of an alternate design of a row of flexible elements, with the elements in a non-biased position, forming a tortuous path therethrough.
Figure 8:
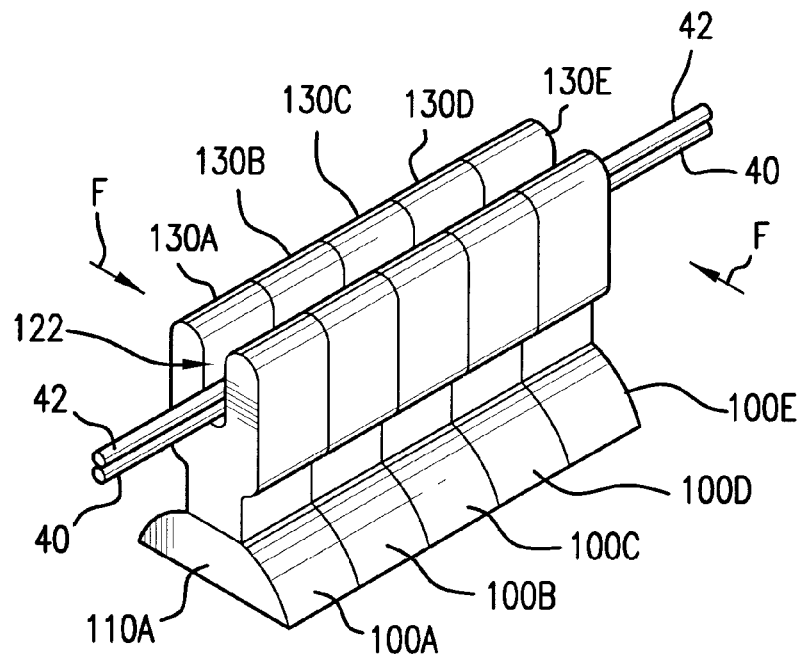
FIG. 8 is a perspective view of the row of elements of FIG. 7, with the elements biased into a first position such that an opening slot forms along the top of the row.
Figure 13:
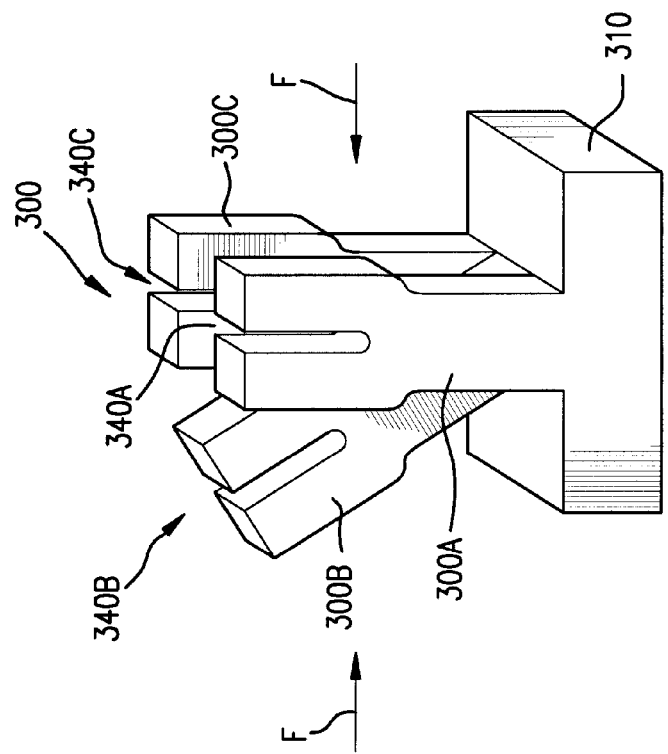
FIG. 13 is an exploded perspective view of an embodiment of the invention having two non-flexible elements with a single flexible element positioned therebetween.

FIGS. 1 to 6 illustrate a first preferred embodiment of the present invention, and FIGS. 7 and 8 illustrate a second preferred embodiment of the present invention. FIGS. 9 to 12 illustrate an exemplary positioning/biasing device for use with various embodiments of a suture clamp. FIG. 13 illustrates an embodiment of the invention having only one flexible element. FIGS. 14 to 18B show component parts of an embodiment of the device having a suture guide assembly, a pair of flexible suture capture elements, and a rail guide. FIGS. 19 to 22 show sequential steps in the deployment of the embodiment of the device shown FIGS. 14 to 18B.

Figure 1:
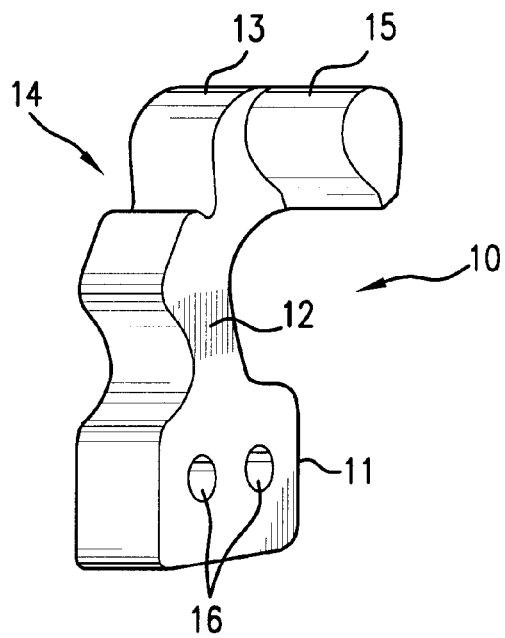
FIG. 1 is a perspective view of a single flexible element.

FIG. 1 illustrates an embodiment of a single clamping element 10. Element 10 has a lower portion 11, a neck 12, and an upper portion 13. A slot 14 is defined by upper portion 13. Also, an optional projection 15 extends longitudinally from upper portion 13. As will be explained, projections 15 provide contact surfaces between adjacent elements such that the elements may rest against one another when in a non-biased (second) position. It is to be understood that projections 15 are optional and that various embodiments of the present invention do not require projections 15 to operate.

Element 10 is preferably fabricated from a unitary block of Nitinol or other suitable flexible or elastic material, including various plastics and metals. Photochemical machining or other known techniques may be used to form element 10. Most preferably, each element 10 will be dimensioned to about 1 mm in height.

Figure 3:
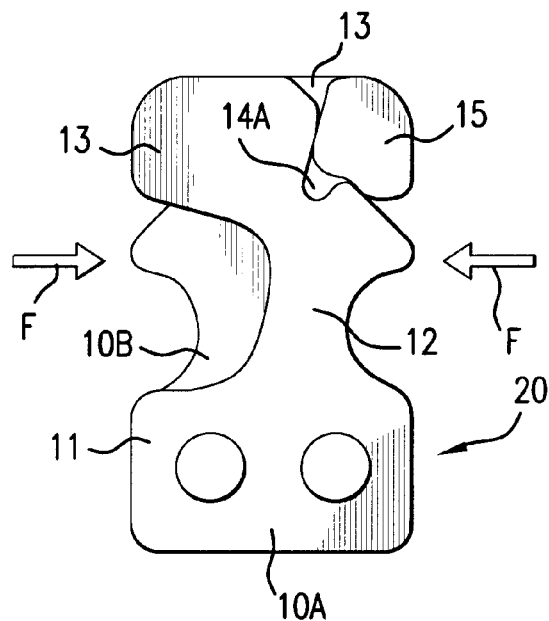
FIG. 3 is an end view of the row of flexible elements as illustrated in FIG. 2.
Figure 2:
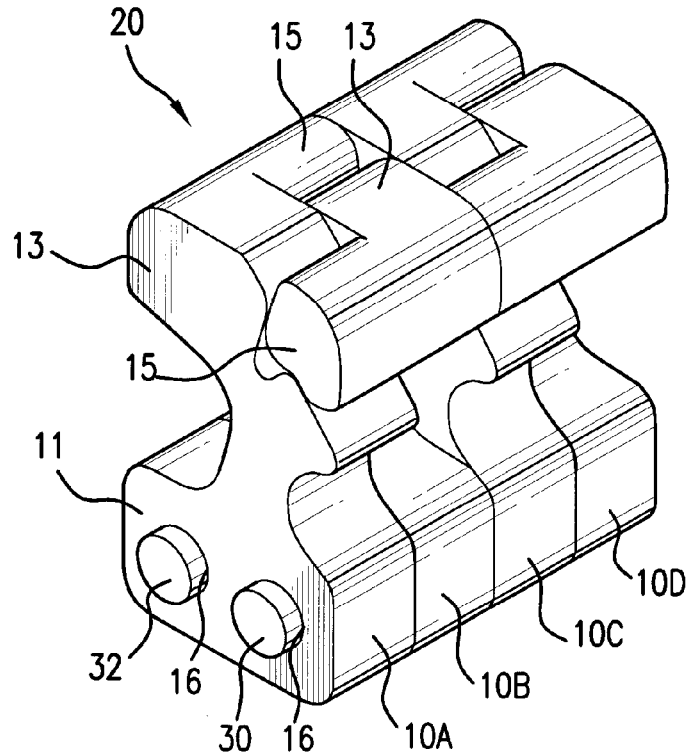
FIG. 2 is a perspective view of row of flexible elements as individually illustrated in FIG. 1, with the elements in a non-biased position, forming a tortuous path therethrough.

As can be seen in FIGS. 2 and 3, a plurality of flexible elements 10 (i.e.: 10A, 10B, 10C, 10D, etc.) can be positioned side-by-side forming row 20. Preferably, lower portions 11 of the successive elements 10 are positioned adjacent to one another such that their projections 15 interlock with upper portions 13 of adjacent elements (as shown in FIG. 2). Lower portions 11 of the successive elements 10 may optionally be connected together (side-by-side) by a variety of techniques, including fusion bonding and adhesives. Alternatively, lower portions 11 of the successive elements 10 may optionally be spaced some distance apart from one another (not shown).

In another embodiment, elements 10 may each optionally comprise a pair of holes 16 (see FIG. 1) such that elements 10A, 10B, 10C, 10D, can be positioned on rods 30 and 32, or a similar mounting element or structure.

In accordance with the present invention, a biasing force ("F" in FIG. 3) is applied to the upper portions of each of elements 10. Biasing force F is applied in a direction generally transverse to the length of the row. Thus, as can be seen, force F will squeeze row 20 from its sides. The bottom portions 11 of each of elements 10 are held in a constant position with respect to one another. Alternatively, an embodiment of the present invention may include a single unitary bottom portion (as opposed to the illustrated plurality of separate bottom portions 11). Thus, the device which comprises the row of elements can be machined or molded out of a solid block of material such that the elements have a common bottom portion (for example, as illustrated in FIG. 13). Having a thin neck 12, the upper portions 13 of each of elements 10 will tend to move apart in a direction transverse to the row of elements as biasing force F is applied.

Figure 4:
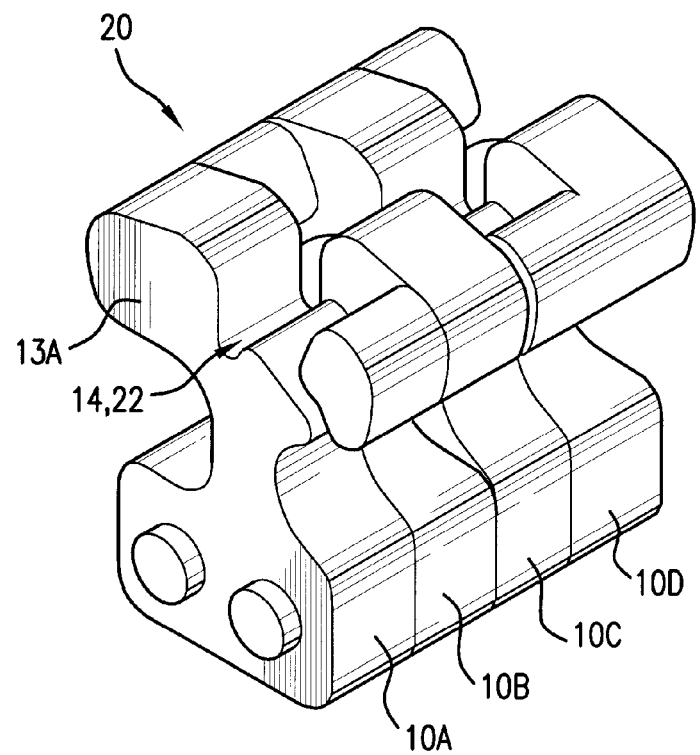
FIG. 4 is a perspective view of row of flexible elements as individually illustrated in FIG. 1, with the elements biased into a first position such that an opening slot forms along the top of the row.

As shown in FIGS. 4 to 6, when a sufficiently strong biasing force F is applied, elements 10 move to a first position in which a slot 22 forms along the top of row 20. (i.e. when adjacent slot defining features 14 in successive elements 10 are in alignment). At this time a pair of sutures 40 and 42 (see FIG. 10) can be positioned within slot 22. When force F is removed, elements 10 will naturally tend to return to their non-biased (or possibly biased against one another) position, at which time an upper portion 13A of a first element (10A)

will abut against projection 15B of upper portion 13B of a second element (10B), as shown in FIGS. 2 and 3.

The flexible elements which are used to form the suture clamping device can be made in a variety of different shapes. For example, referring to FIGS. 7 and 8, a row 200 of flexible elements 100A, 100B, 100C, 100D, 100E, etc. are used to form a suture clamping device. Specifically, as shown in the non-biased position (i.e. FIG. 7), elements 100 each have a lower portion 110, a neck 120 and an upper portion 130. Upper portion 130 has a slot defining features 140 formed therein. As can be seen, element 110 is formed such that its neck 120 holds upper portion 130 (and slot defining features 140) at an angle when in the non-biased (FIG. 7) position.

Thus, when a squeezing force F is applied against flexible elements 100 on either side of row 200, elements will be biased into the position shown in FIG. 8 wherein the slot-defining features 140 of successive elements are positioned in alignment with one another to form a slot 122. A pair of sutures 40 and 42 can then be placed into slot 122. When the biasing force F is released, elements 110 will tend to move back to the position shown in FIG. 7, thus forming a tortuous path for sutures 40 and 42, passing therethrough.

In an alternate embodiment, the elements are formed such that a suture slot is instead formed when the elements are in their non-biased position. In such an embodiment, the application of a biasing force would move the elements into a position such that the tortuous suture path is formed therethrough. After the elements have been biased to move into positions forming the tortuous suture path therethrough, a clip or other fastening device can be used to hold the elements in the biased position, with the tortuous suture path passing therethrough.

Sutures 40 and 42 may preferably comprise opposite ends of a continuous suture loop which has been used to suture together an anastomosis graft or to close a hole in a blood vessel or other tissue wall, or to anchor one or more suture elements. Alternatively, sutures 40 and 42 may comprise ends of separate suture strands which are fastened (i.e. clamped) together by present invention.

Figure 9:
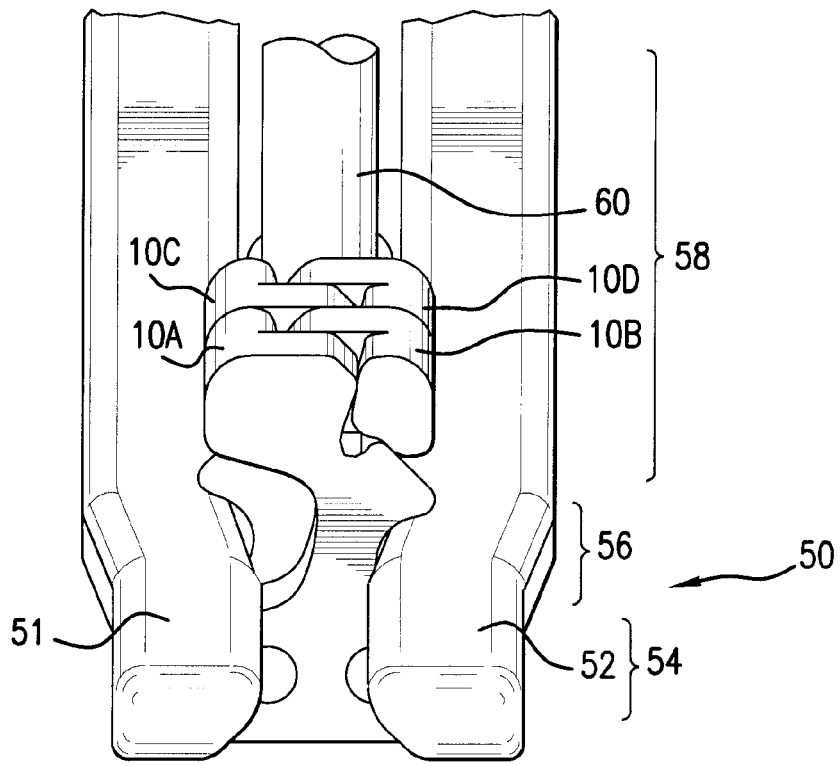
FIG. 9 is a perspective end view of a dual rail biasing device slidably received over the row of flexible elements, with the elements in a non-biased position, as shown in FIGS. 2 and 3.

In accordance with preferred aspects of the present invention, a method for clamping a suture pair is also provided. Preferably, this method includes biasing the row of adjacent flexible elements 10 (i.e.: applying force F) so that elements 10 move to the position (as shown in FIGS. 4 to 6) in which an opening slot 22 is formed therethrough. Preferably, this biasing force is applied in a direction transverse to the length of the row. Then, suture pair 40 and 42 is received into opening slot 22. Then, biasing force F is removed such that the adjacent flexible elements 10A, 10B, 10C, 10D, etc., move to positions which hold the suture pair in a tortuous path (as shown in FIGS. 2 and 3). Similarly, as seen in FIGS. 7 and 8, the present method may comprise: biasing the row of adjacent flexible elements 100 (i.e.: applying force F) so that elements 100 move to the first position (as shown in FIG. 9) in which an opening slot 122 is formed there along. Then, suture pair 40 and 42 is received into opening slot 122. Then, biasing force F is removed such that the adjacent flexible elements 100A, 100B, 100C, 100D, etc., move or spring back to positions which hold the suture pair in a tortuous path (as shown in FIG. 7).

The present method will be explained by reference to a dual rail positioning/biasing device shown in FIGS. 9 to 12, as follows.

A biasing device 50 may be provided as part of the present suture clamping system. In one embodiment, biasing device 50 comprises two rails 51 and 52 which are parallel to one another over two regions, and angled with respect to one another over another region. Specifically, as seen in FIG. 9, rails 51 and 52 are parallel with respect to one another in regions 54 and 58 and are angled with respect to one another in region 56. As also seen in FIG. 9, a push rod 60 is used to successively push elements 10A, 10B, 10C and 10D distally from region 58, and then through regions 56 and 54.

Figure 11:
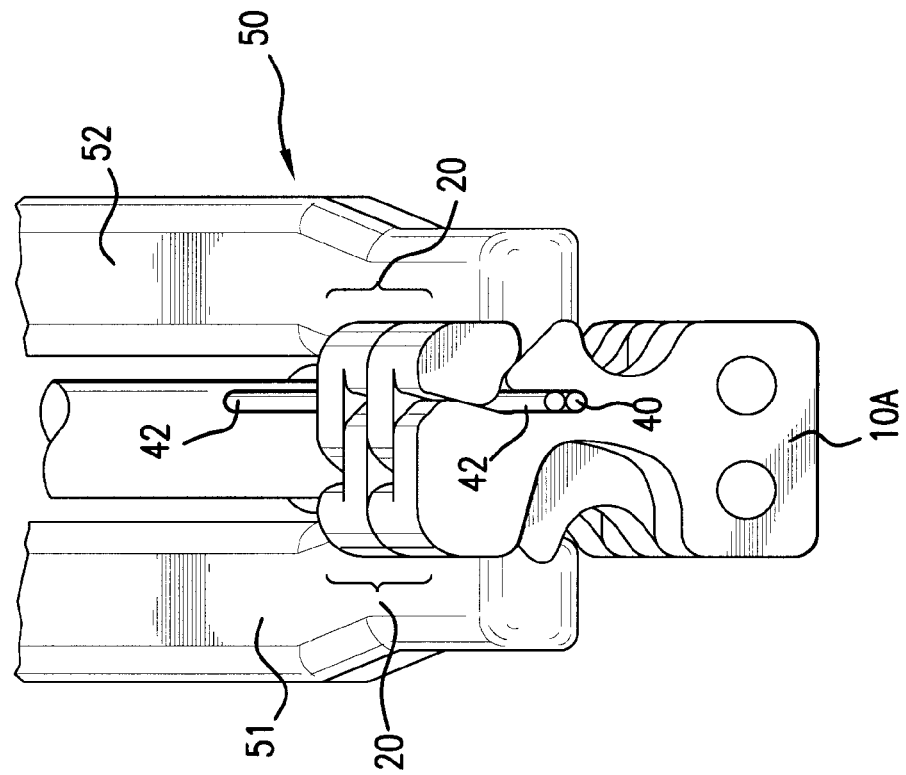
FIG. 11 is a perspective end view of the row of flexible elements after it has been pushed fully through the dual rail biasing device, such that the elements return to a non-biased position, trapping the suture pair in a tortuous path therein, as shown in FIGS. 2 and 3.
Figure 10:
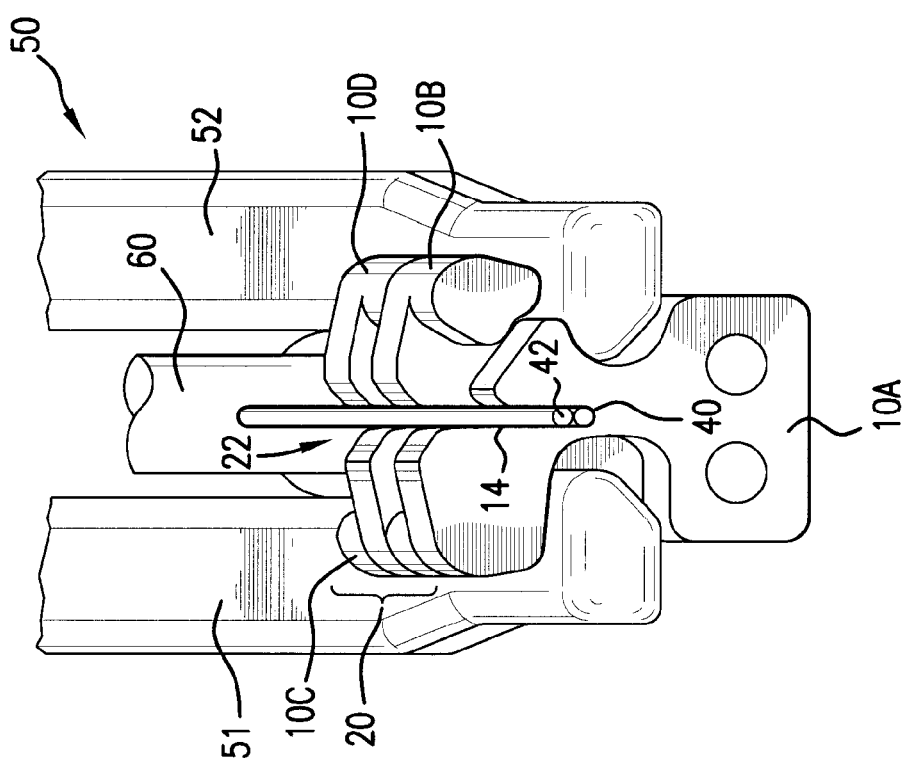
FIG. 10 is in a view similar to FIG. 9, but including as suture pair received in the slot formed through the row of elements.
Figure 12:
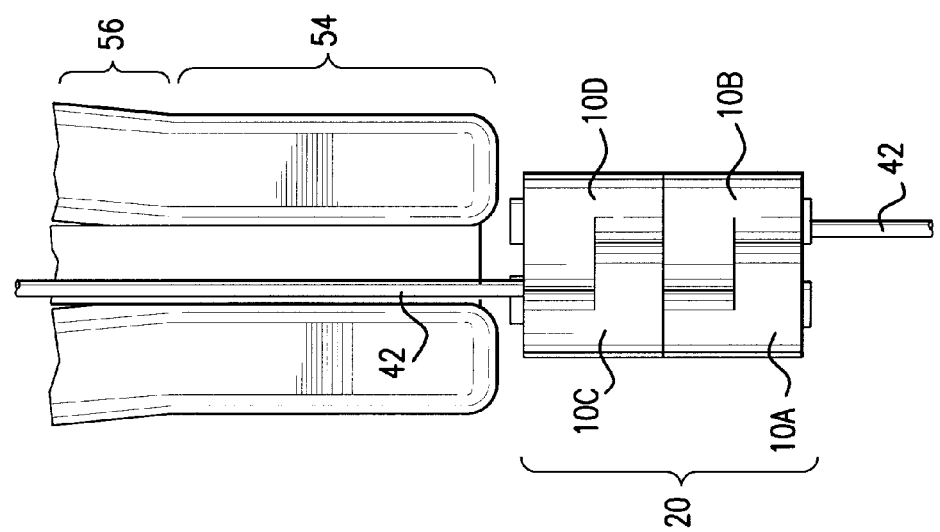
FIG. 12 is a top plan view corresponding to FIG. 11.
Figure 14:
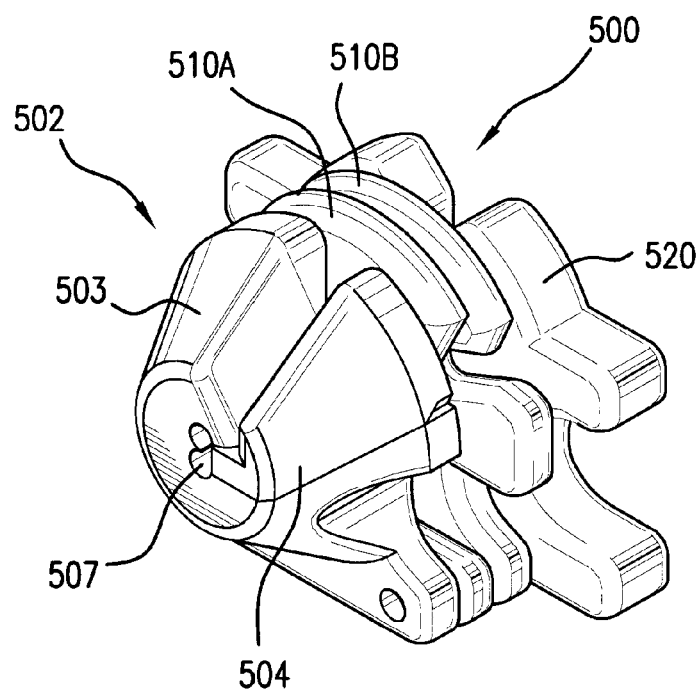
FIG. 14 is a perspective view of an embodiment of the invention further comprising a suture guide assembly, a pair of flexible suture capture elements and a rail guide.
Figure 15:
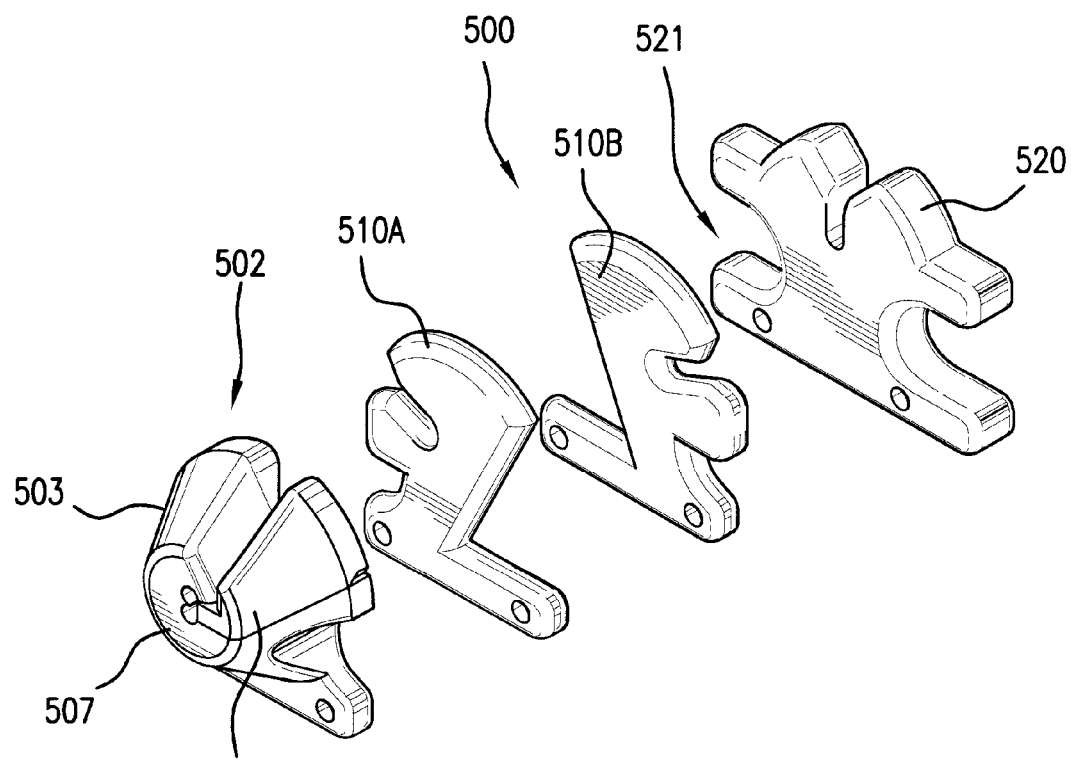
FIG. 15 is an exploded perspective view of the invention shown in FIG. 14.
Figure 16A:
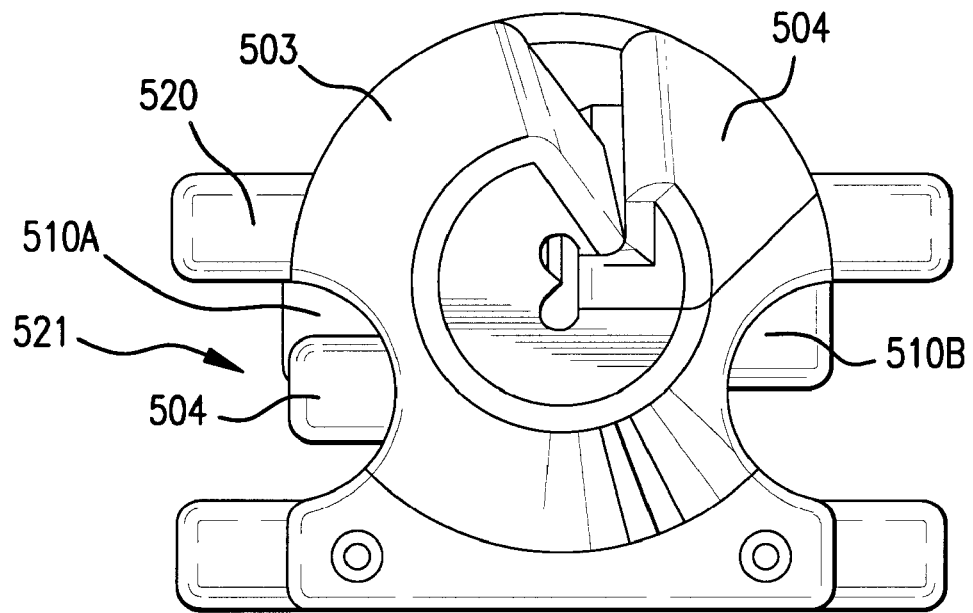
FIG. 16A is a front elevation view of the embodiment of the invention shown in FIG. 14 in a closed position.
Figure 16B:
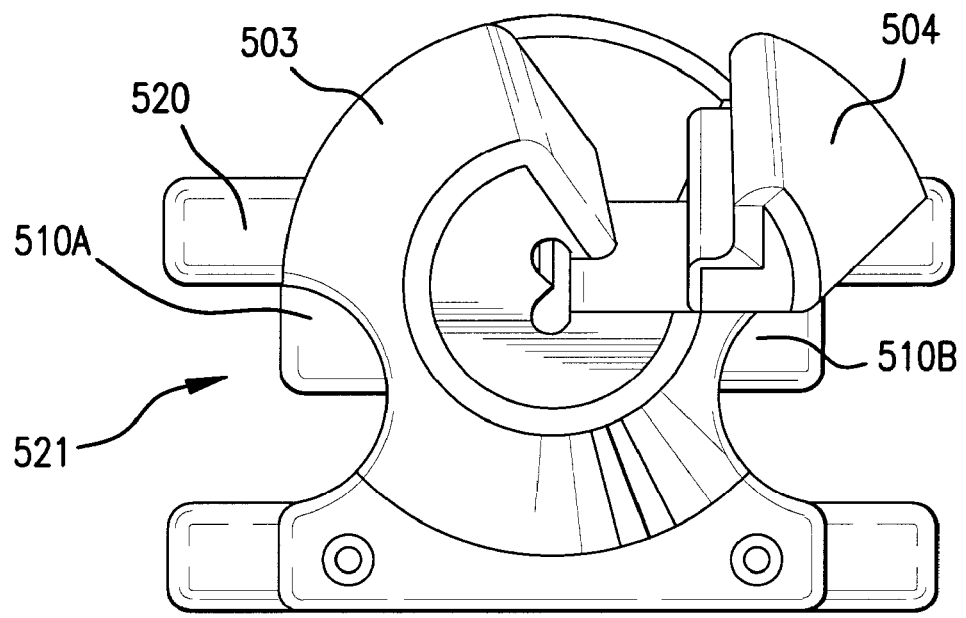
FIG. 16B is a front elevation view of the embodiment of the invention shown in FIG. 14 in an open position.
Figure 17A:
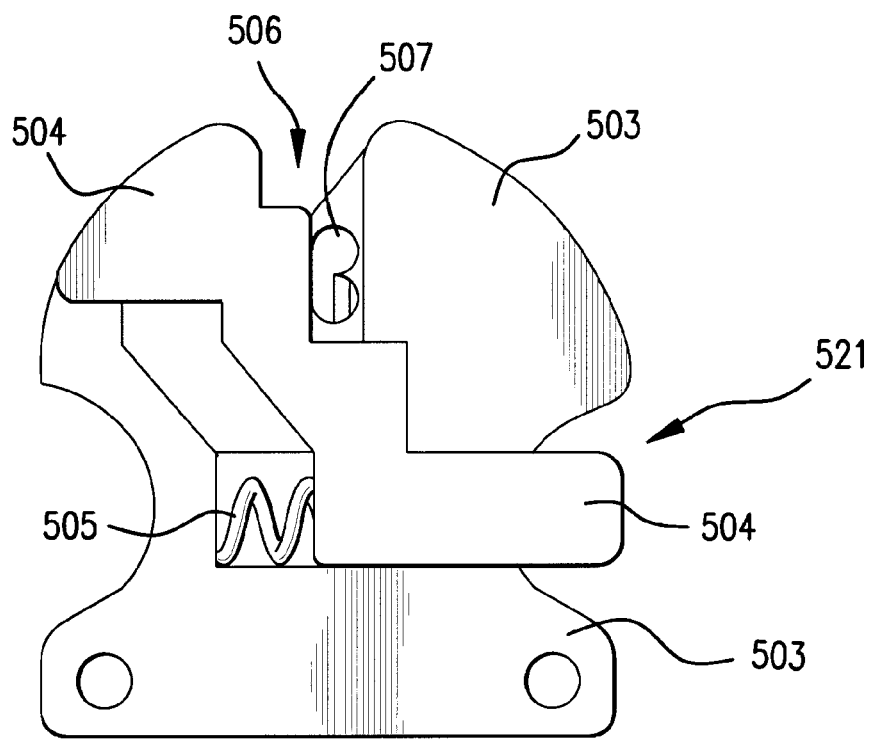
FIG. 17A is a rear view of the suture guide assembly in a closed position (corresponding to FIG. 16A).
Figure 17B:
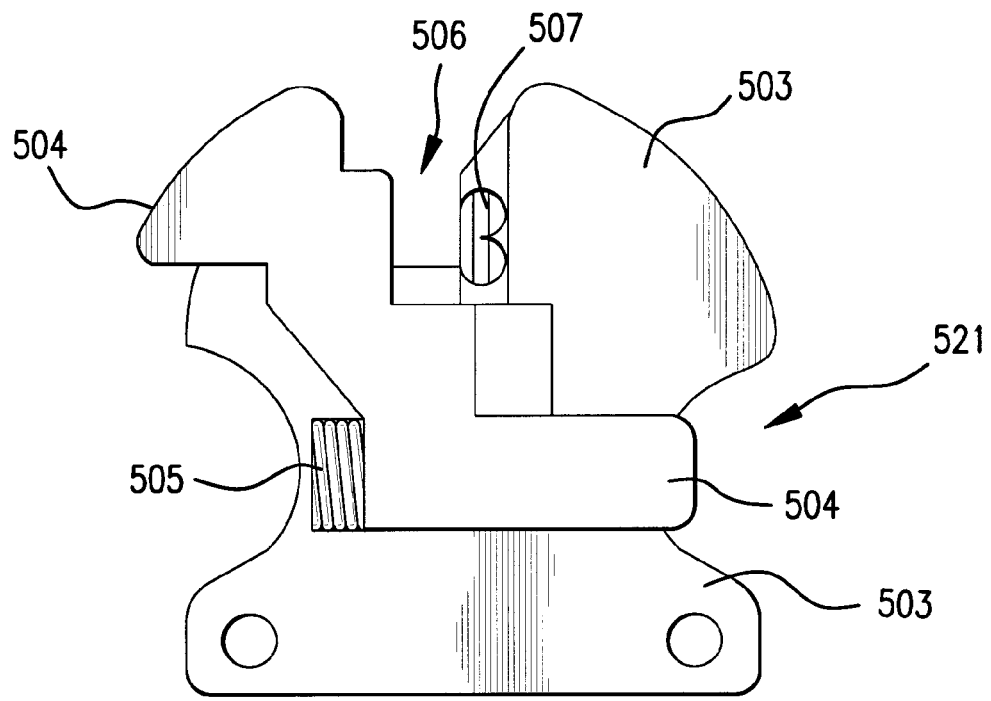
FIG. 17B is a rear view of the suture guide assembly in an open position (corresponding to FIG. 16B).

From the position shown in FIG. 9, push rod 60 is advanced such that row 20 of elements 10 is pushed into region 54 (as shown in FIG. 10) wherein rails 51 and 52 are positioned closer together, such that individual slot defining features 14 are put into alignment (forming slot 22 along the length of row 20). As shown in FIG. 10, a suture pair 40, 42 can then be positioned within slot 22. Lastly, as shown in FIGS. 11 and 12, row 20 is pushed out of the distal end of biasing device 50. As shown in FIG. 12, the biasing force on the sides of row 20 is removed such that elements 10A, 10B, 10C and 10D return to their non-biased position, thus forming a tortuous path for suture pair 40 and 42 passing therethrough.

As stated above, the present invention may comprise a plurality of flexible elements. It is to be understood, however, that embodiments of the invention may also comprise non-flexible elements, or various combinations of flexible and non-flexible elements. For example, as shown in FIG. 13, a row 300 of elements (which may optionally have a single unitary base 310) may have a single flexible element 300B disposed between (or otherwise adjacent to) non-flexible elements 300A and 300C. When a biasing force F is applied to the sides of the device, flexible element 300B will move to a position such that elements 300A, 300B and 300C will be placed in alignment. Then, a suture, or suture pair can easily be threaded through opening slots 340A, 340B and 340C. When biasing force F is removed, element 300B will tend to spring back into the position shown in FIG. 13, thereby forming a tortuous path, firmly holding the suture(s) therein.

FIGS. 14 to 18B show an alternate embodiment of the present invention that includes a suture clamp assembly 500 including a suture guide assembly 502, a pair of flexible elements 510A and 510B and a rail guide 520. Suture guide assembly 502 includes a suture guide 503 and a suture lock 504. As can be seen in FIGS. 16A to 17B, suture lock 504 is movable with respect to suture guide 503, thus permitting a suture or suture pair to be inserted therebetween, and then clamped, as follows. As shown in FIGS. 16A and 17B, suture lock 504 is initially position adjacent to suture guide 503 (by the action of spring 505). When using the device, the end of suture lock 504 which extends in to cavity 521 in rail guide 520 is pushed. Such force compresses spring 505 so that suture lock 504 moves to the position shown in FIGS. 16B and 17B, thereby opening passageway 506, permitting a suture, or suture pair to be inserted therein. Thereafter, the force can be removed from the end of suture lock 504 which extends in to cavity 521 such that, spring 505 expands and suture lock 504 returns to the position shown in FIGS. 16A and 17A, thereby trapping a suture or suture pair in passageway 506.

Figure 18A:
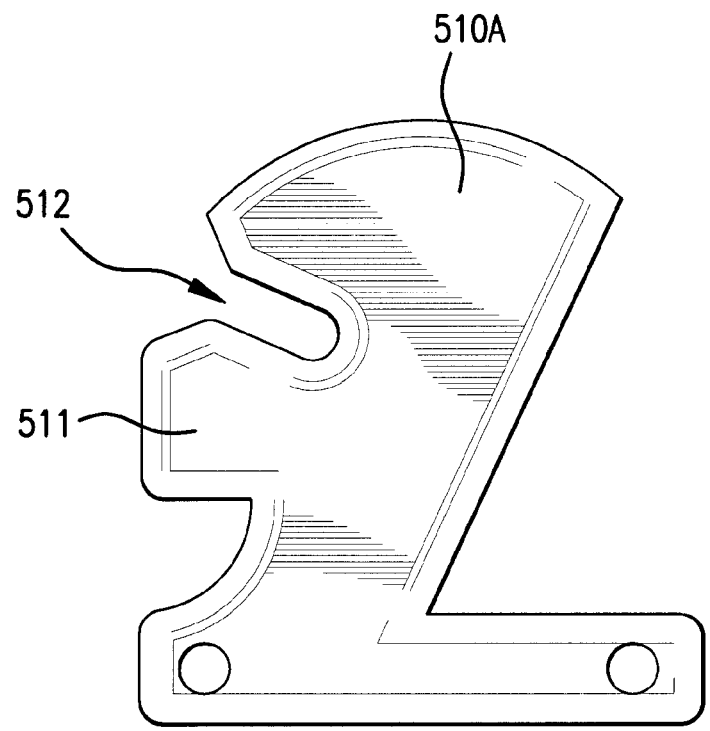
FIG. 18A is a front view of a pair of suture capture elements in a non-biased position.

Behind suture guide assembly 502 are positioned one or more flexible elements which are used to capture a suture or suture pair. These flexible elements operate in the same manner as the "row of flexible elements" described with regard to other embodiments herein. Specifically, flexible elements 510A and 510B have a non-biased position as shown in FIG. 18A. When a biasing force is applied to the underside of projections 511, flexible elements 510A and 510B move to the positions shown in FIG. 18B, at which time their slots 512 move into alignment with one another. When slots 512 of flexible elements 510A and 510B are positioned in alignment, a suture or suture pair can be received therein. Then, the biasing forces can be removed from projections 511, causing the flexible elements to move towards the position shown in FIG. 18A, thereby forming a tortuous path for a suture passing therethrough. It is to be understood that the present invention encompasses embodiments with more than two flexible suture capture elements 510, or even as few as one flexible and one non-flexible element.

In optional preferred aspects, both the suture guide 503 and the suture lock 504 are dimensioned such that the opening slot 507 (formed in passageway 506 in which the suture(s) are trapped) is not co-linear with the opening slots 512 through flexible elements 510A and 510B. An advantage of opening slot 507 not being co-linear with the path through opening slots 512 is that this further adds to the tortuosity of the suture path through the device, and permits more exact positioning of the device with respect to the target tissue.

Figure 18B:
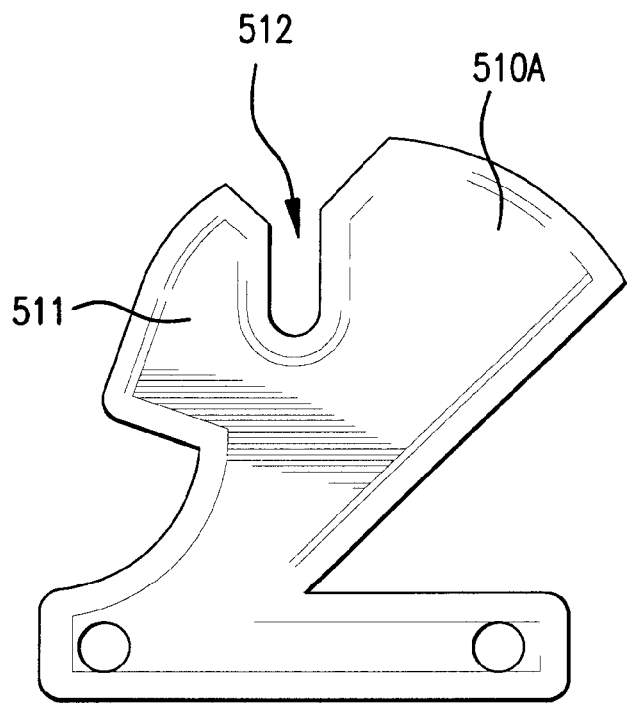
FIG. 18B is a front view of a pair of suture capture elements in a biased position, thus forming a suture opening therethrough.
Figure 19:
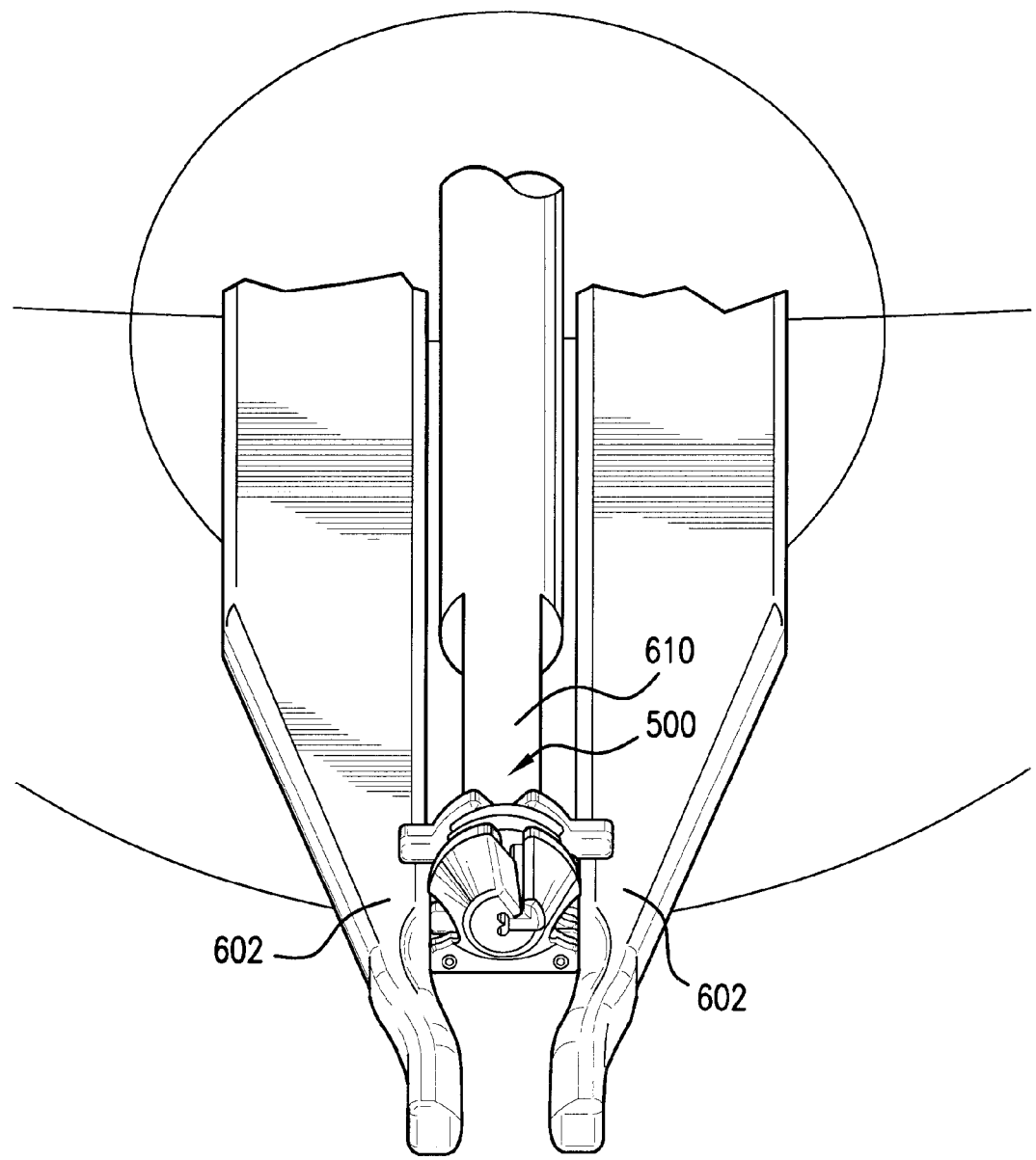
FIG. 19 is a top perspective view of the device of FIG. 14, positioned on a pair of rails prior to deployment.
Figure 20:
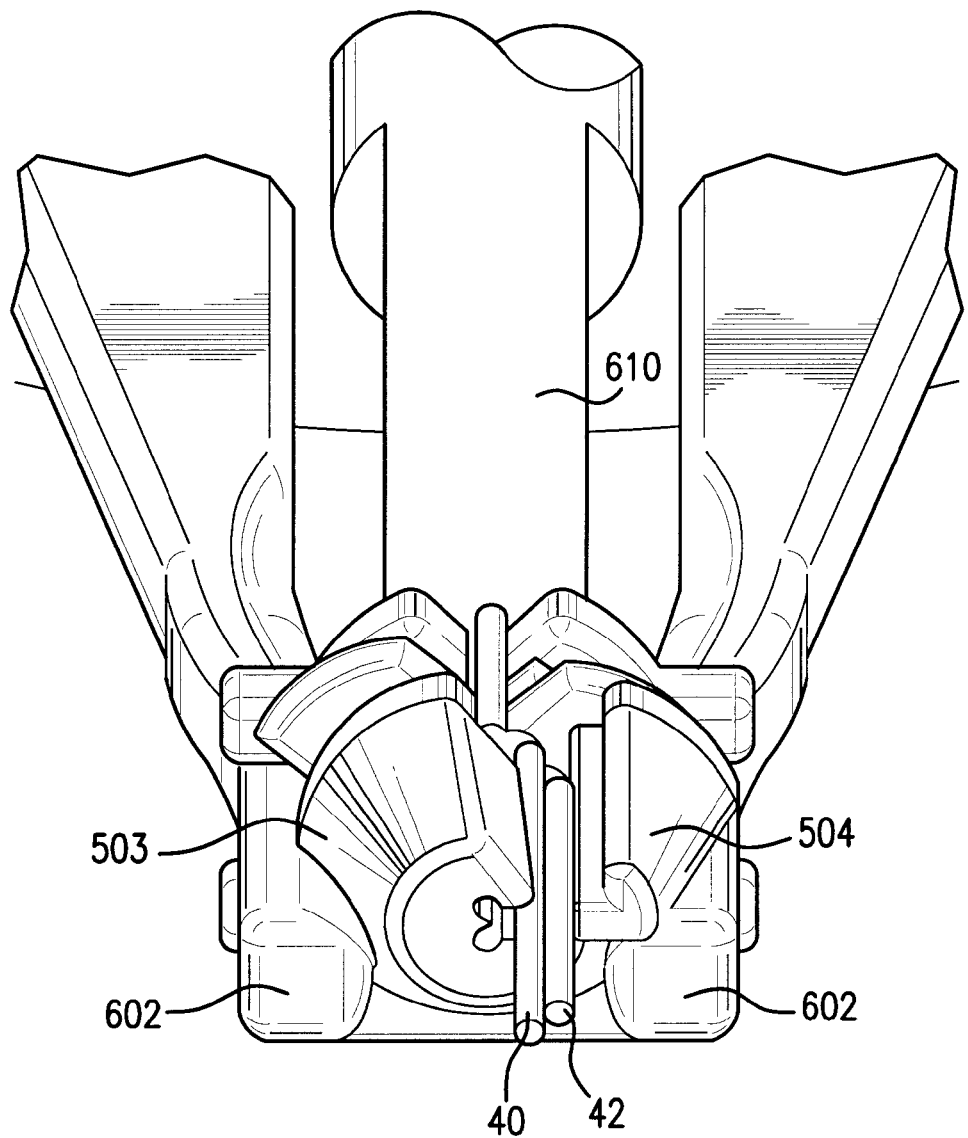
FIG. 20 is a view similar to FIG. 19, but with the device advanced to a position such that the rails cause the device to open to receive a suture pair therein.
Figure 21:
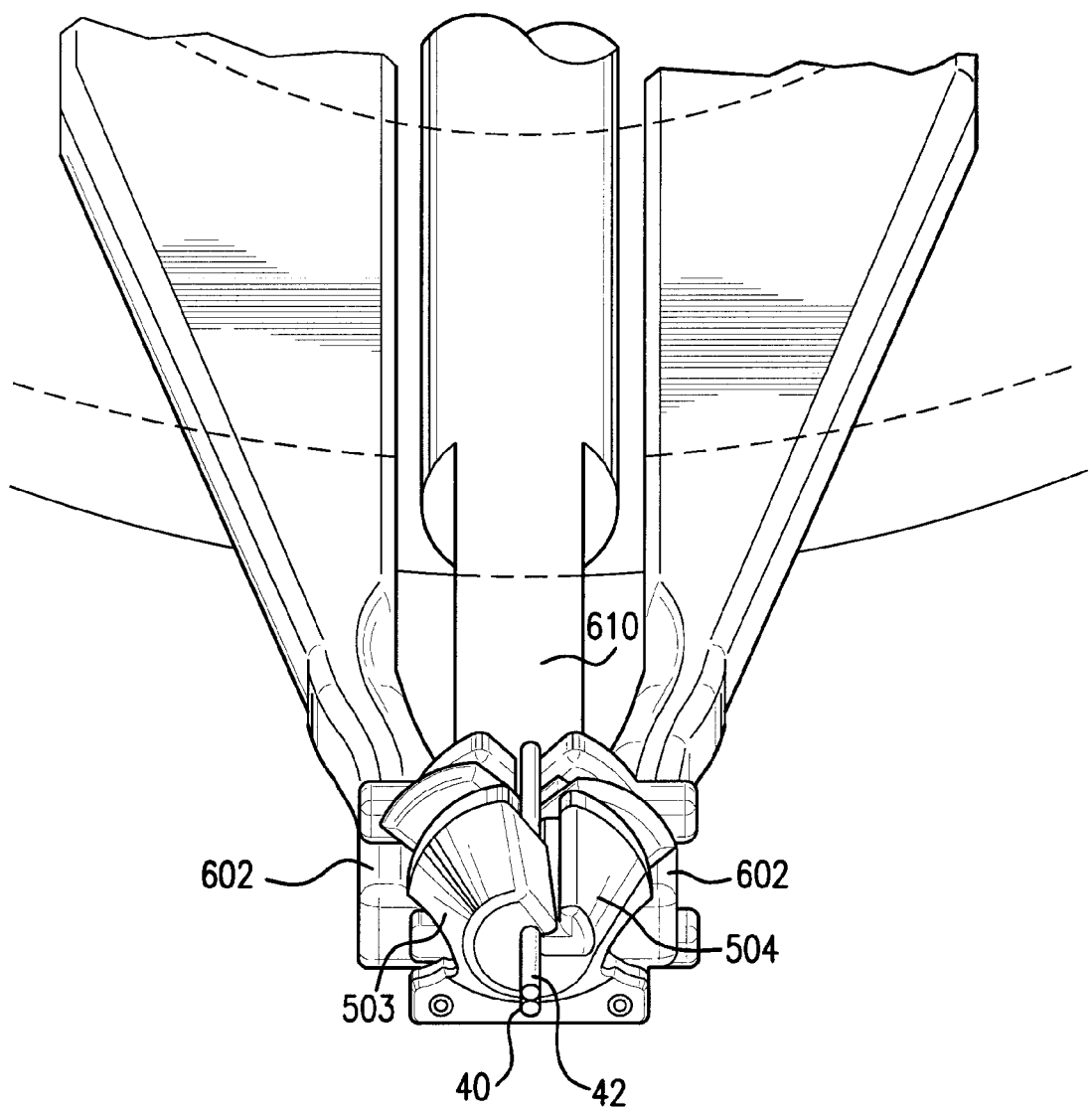
FIG. 21 is a view similar to FIG. 20, but with the device advanced to a position such that the suture guide assembly projects beyond the distal ends of the rails, showing the suture guide assembly locking onto the suture pair.
Figure 22:
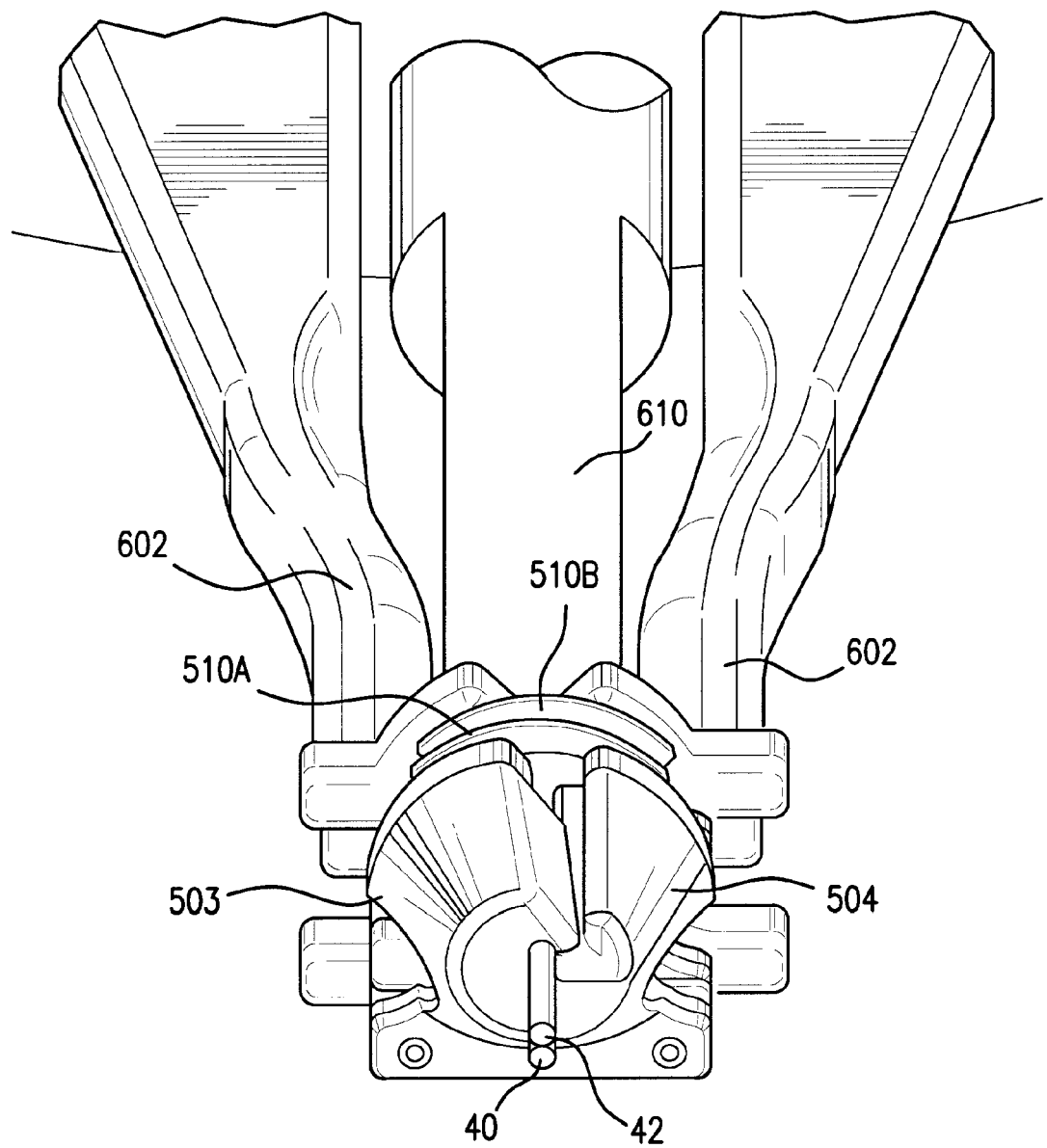
FIG. 22 is a view similar to FIG. 21, but with the entire device advanced beyond the distal ends of the pair of rails, showing the suture capture elements locking onto the suture pair.

FIGS. 19 to 22 show the deployment of the embodiment of the invention shown in FIGS. 14 to 18B, as follows. As shown in FIG. 19, suture clamp assembly 500 is initially positioned between rails 602, with a push rod 610 abutting against the rear of rail guide 520. Next, push rod 610 is used to advance the suture clamp assembly 500 to the position shown in FIG. 20 where the spacing between rails 602 narrows. Thus, one of the rails 602 will push on the end of suture lock 504 in cavity 512 so that suture lock 504 moves apart from suture guide 503, as explained above. In addition, advancing flexible elements 510A and 510B to the region where the spacing of rails 602 narrows will move flexible elements 510A and 510B to their biased position (FIG. 18B). At this time, a pair of sutures 40 and 42 can be received therein. Next, push rod 610 is used to advance the suture clamp assembly 500 to the position shown in FIG. 21 where suture guide assembly 502 is advanced beyond the distal end of the rails 602. Accordingly, suture lock 504 moves back into position against suture guide 503, thereby trapping sutures 40 and 42 therebetween. Lastly, as shown in FIG. 22, push rod 610 is used to fully push assembly 500 out beyond the distal end of rails 602. At this time, flexible elements 510A and 510B spring back to their non-biased positions, thus forming a tortuous path for sutures 40 and 42 passing therethrough. Accordingly, the row of flexible elements 510A and 510B assist suture guide assembly 502 in clamping onto sutures 40 and 42, thereby operating as a system which fastens the sutures together. In accordance with this embodiment of the invention, the suture guide assembly 502 fastens onto the suture (or suture pair) prior to flexible elements 510A and 510B fastening onto the suture(s). The suture guide assembly 502 can be positioned immediately adjacent to the tissue target site, if desired. After the suture guide assembly 502 has clamped onto the suture(s), the flexible elements 510A and 510B will sequentially clamp onto the suture(s), thereby taking up any slack in the suture(s) from the proximal side of the device. In other words, as each of the elements in the row of flexible elements is sequentially pushed out from between rails 602, the flexible elements will sequentially move to their non-biased positions, drawing in suture through rail guide 520. Since the suture is pulled in from the rail guide (i.e. the proximal) end of the device, it will not pull on the suture(s) from the suture guide assembly (i.e. the distal) end of the device. This minimizes inadvertent pulling on the sutures at the target tissue location (i.e. at the distal) end of the device).

The present system can be positioned directly adjacent to the operative site at which it is desirable to secure the suture pair. Specifically, the present system can be deployed without pulling suture at the surgical site as the suture pair is secured together. Rather, in preferred embodiments, as the present system is deployed, it pulls in suture from end of the clamp positioned away from the operative site. In contrast, manual or even automatic knot tying systems may either result in a loose knot being positioned at a small distance away from the operative site, or an overly tight knot pulling excessively on the tissues.

In addition, the present system can minimize the extent to which suture at the surgical site is pulled as it secures the suture(s). As the present system is deployed, it simply tightens together a suture pair at the operative site. In contrast, when tying together a suture pair, it is typically difficult to tie a knot very close to the operative site without excessively pulling on the tissues being tied together.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture clamp comprising a plurality of individual elements positioned together in a row, each individual element comprising a lower portion, a flexible neck extending from the lower portion, and an upper portion having a slot, the plurality of slot portions of the plurality of individual elements defining a slot sized to accept a suture element through the row of individual elements when the individual elements are biased into a first position with the plurality of slot portions longitudinally aligned, the flexible necks of adjacently positioned individual elements moved towards one another in a direction transverse to the longitudinal slot and the upper portions of adjacently positioned individual elements moved apart in the direction transverse to the longitudinal slot, the plurality of slot portions define a tortuous path for the suture element when at least one of the individual elements is unbiased to a second position with a portion of the upper portion of one individual element resting against the upper portion of an adjacently positioned individual element and the flexible necks of adjacently positioned individual elements being moved away from one another in the direction transverse to the longitudinal slot, the tortuous path preventing passage of the suture through the slot portions of adjacently positioned separate elements.

2. The suture clamp according to claim 1, wherein one or more of the individual elements are flexible.

3. The suture clamp according to claim 1, wherein the suture clamp is constructed of nitinol.

4. The suture clamp according to claim 1, wherein the plurality of elements are bonded together to form a single suture clamp.

5. The suture clamp according to claim 1, wherein the plurality of individual elements are sized to receive a second suture element therethrough.

6. The suture clamp according to claim 5, wherein the first and second suture elements comprise ends of a suture loop.

7. The suture clamp according to claim 1, wherein the plurality of separate elements are generally identically shaped.

8. A suture clamp comprising a plurality of separate modular, non-integrally formed elements positioned adjacently together in a row, each separate modular element comprising an upper portion having a slot adapted to receive a suture element, a flexible neck extending from the upper portion, and a lower portion extending from the flexible neck, the plurality of slots of the plurality of separate modular elements configured to accept the first suture element through the row of separate modular elements when the separate modular elements are biased to a first position with the plurality of slots being longitudinally aligned, the flexible necks of adjacently positioned separate modular elements moved towards one another in a direction transverse to the longitudinal slot and the upper portions of adjacently positioned separate modular elements moved apart in the direction transverse to the longitudinal slot, the plurality of slots define a tortuous path for the first suture element when at least one of the separate modular elements is unbiased in a second position where the upper portions of adjacent separate modular elements are moved toward one another in the direction transverse to the longitudinal slot, the tortuous path preventing passage of the suture through the slots of adjacently positioned separate elements.

9. The suture clamp according to claim 8, wherein the flexible element is in the first position when biased.

10. The suture clamp according to claim 8, wherein the suture clamp is constructed of nitinol.

11. The suture clamp according to claim 8, wherein the plurality of elements are bonded together to form a single suture clamp.

12. The suture clamp according to claim 8, wherein the plurality of elements are sized to receive a second suture element therethrough.

13. The suture clamp according to claim 12, wherein the first and second suture elements comprise ends of a suture loop.

14. The suture clamp according to claim 8, wherein the plurality of separate elements are generally identically shaped.

15. A method of clamping a suture passing through a tissue layer with a suture clamp system comprising a plurality of separate, non-integrally formed elements positioned together in a row along a pair of rods, each separate element comprising an upper portion having a slot portion, the separate element further including a flexible neck extending from the upper portion to a lower portion, wherein the separate elements are such that when at least one of the separate elements is biased into a first position, the plurality of slot portions of the plurality of separate elements define a slot to accept a suture is formed through the row of individual elements, and the plurality of slot portions defining a tortuous path through the separate elements when the separate elements are not biased, the tortuous path preventing passage of the suture through the slot portions of adjacently positioned separate elements, the method comprising:

applying a biasing force to the at least one separate element to bias at least one separate element into the first position from a second position, the first position having the slot portion of the at least one separate element longitudinally aligned with the slot portion of an adjacently positioned another at least one separate element, the flexible necks of adjacently positioned separate elements moved towards one another in the direction transverse to the longitudinal slot, the upper portions of adjacently positioned separate elements moved apart in the direction transverse to the longitudinal slot, the second position having the separate elements defining the tortuous path and preventing passage of the suture through the slot portions of adjacently positioned separate elements, passing the suture through a tissue layer, receiving the suture into the slots of the plurality of separate elements, and removing the biasing force to move the at least one separate element to form the tortuous path to secure the suture passing through the slot portions of the plurality of separate elements within the suture clamp system and to move the upper portion of the at least one separate element toward the upper portion of an adjacently positioned separate element in the direction transverse to the longitudinal slot.

16. The method according to claim 15, wherein the biasing step comprises using a biasing device to bias the at least one separate element.

17. The method according to claim 16, wherein the receiving step comprises receiving two sutures into the slot.

18. The method according to claim 15, wherein the biasing step comprises biasing in a direction transverse to a length of the row.

19. The method according to claim 15, further comprising securing the row of separate elements to the suture.

20. The method according to claim 15, wherein the step of removing the biasing comprises slidably advancing the row of separate elements through a biasing device.

* * * * *